United States Patent [19]

Hubbs et al.

[11] Patent Number: 5,322,931

[45] Date of Patent: Jun. 21, 1994

[54] PROCESS FOR SYNTHESIZING PEPTIDES - FRAGMENT CONDENSATION

[75] Inventors: John C. Hubbs; Stephen W. Parker, both of Kingsport, Tenn.

[73] Assignee: Eastman Kodak Company, Rochester, N.Y.

[21] Appl. No.: 965,627

[22] Filed: Oct. 22, 1992

Related U.S. Application Data

[63] Continuation of Ser. No. 558,121, Jul. 24, 1990, abandoned.

[51] Int. Cl.$^5$ .............................................. C07K 5/00
[52] U.S. Cl. .................................. 530/333; 530/335; 530/338; 530/339; 530/344; 530/412
[58] Field of Search ............... 530/333, 335, 338, 339, 530/344, 412

[56] References Cited

U.S. PATENT DOCUMENTS 4,774,319  9/1988  Ono et al. ........................... 530/324
4,880,778  11/1989  Bowers et al. ........................ 514/12

FOREIGN PATENT DOCUMENTS

WO89/07110  8/1989  PCT Int'l Appl. .
WO89/07111  8/1989  PCT Int'l Appl. .
WO89/10933  11/1989  PCT Int'l Appl. .

OTHER PUBLICATIONS

Gross & Meinhofer, *The Peptides*, vol. 2 (Academic Press, 1980) Pp. 287–289.
M. Bodanszky, *Principles of Peptide Syntheses* (Springer-Verlag (1984) 208–210.
M. Bodanszky, Intl. J. Pept. Prot. Res. vol. 25 (1985) 449–474.

*Primary Examiner*—F. T. Moezie
*Attorney, Agent, or Firm*—Betty J. James; William P. Heath, Jr,

[57] ABSTRACT

A solution phase process for making peptides having biological activity or peptide intermediates which can be used to prepare peptides having biological activity is described. The process involves the condensation reaction of two peptide fragments.

17 Claims, No Drawings

PROCESS FOR SYNTHESIZING PEPTIDES - FRAGMENT CONDENSATION

This is a continuation of copending application Ser. No. 07/558,121 filed on Jul. 24, 1990 now abandoned.

This invention relates to a solution phase method for producing peptides having biological activity or peptide intermediates which can be used to prepare peptides having biological activities. Preferably, this invention relates to a method for synthesizing peptides, or peptide intermediates, having growth hormone-releasing activity when administered to animals.

Proteins are composed of amino acids linked together by peptide bonds. Amino acids can be of the type found in protein of biological sources (referred to as naturally occurring amino acids regardless of how produced) or they can be synthesized chemically without having a biological counterpart (referred to as synthetic amino acids). Peptides made from amino acids of either the naturally occurring types or the synthetic type have a variety of uses.

Alpha amino acids typically have one asymmetric carbon atom and are able to rotate the plane of polarized light in either a right-handed (dextrorotatory) or left-handed (levorotatory) direction. Dipeptides can therefore exist as either one or the other (or a mixture) of the two diastereomeric forms. Each of the diastereomeric forms can exist as either one or the other (or as a pair) of two enantiomeric forms. For larger peptides, the possible number of diastereomeric and enantiomeric forms typically grows exponentially with the number of amino acid residues. For various applications, particularly for biological activity, it is often desirable to have only one of the diastereomeric and enantiomeric forms. For example, in living organisms one typically finds only L-amino acids.

Racemization at amino acid residues often occurs during the synthesis of peptides. Such racemization (generation of one or more amino acid residues in both D and L form) generally results in a significant portion of the final peptide being in a biologically inactive form.

Consequently, processes which can produce a peptide in a single diastereomeric form and a single enantiomeric form are highly desirable.

Stewart and Young, Solid Phase Peptide Synthesis (Second Edition, Pierce Chemical Co., Rockford, Ill.) (1984) describe a method of preparing peptides using solid phase technology.

The conventional manner of preparing peptides by solid phase synthesis has the synthesis proceeding in a stepwise manner from the C-terminal end of the peptide. By careful selection of urethane protecting groups for the amino acids used in the stepwise synthesis, racemization can be minimized or eliminated. The starting material can be prepared, for example, by attaching a protected alpha-amino acid to a chloromethylated resin, a hydroxymethyl resin, a benzylhydrylamine (BHA) resin or a para-methylbenzylhydrylamine (p-Me-BHA) resin. After the initial attachment, the alpha-amino protecting group can be removed by acidic reagents, including trifluoroacetic acid (TFA) or hydrochloric acid (HCl) solutions in organic solvents at room temperature. After the removal of the alpha-amino protecting group, the remaining protected amino acids can be coupled stepwise in the desired order. After the desired amino acid sequence has been completed, the resultant peptide can be cleaved from the resin by treatment with a reagent such as hydrogen fluoride (HF). This method is inefficient and costly when one wants to produce large-scale amounts of the peptides.

Although solution phase methods have been known, these methods generally follow the same procedure as that described above with respect to solid phase, namely, a stepwise method in which the synthesis is commenced from the C-terminal end of the peptide and each amino acid sequence is added residue by residue. Such a C to N terminal synthesis is slow and time consuming. Furthermore, one still needs to be concerned about the problem of racemization and yield. Although methods exist to minimize racemization, such methods can have detrimental effects on the flexibility of the general approach and on the resultant yield.

Stepwise synthesis from the N-terminal residue could be an economic and attractive approach. In fact, this is the strategy used in vivo for the synthesis of protein in the ribosomes. However, such strategies have not resulted in successful, practical synthesis of peptide chains. This is because of the problems in racemization that occur at the C-terminal residues of the intermediates during activation and coupling. Accordingly, in the coupling steps and in each further coupling step instead of optically active products, a mixture of diastereoisomers are frequently formed. Thus, such a synthesis is not generally practical.

It would be useful to have a simple method for synthesizing peptides, which have biological activity or are intermediates to peptides having biological activity, that is simple, relatively inexpensive and can be used in large scale production of peptides more conveniently than standard methods.

It would also be useful if there was a method that could produce such peptides in high yields and/or with a low level of racemization.

SUMMARY OF THE INVENTION

We have now discovered a method for synthesizing peptides having biological activity or peptides which are intermediates for biologically active peptides. This method comprises condensing the peptide fragment $X-A_2-Y$ with the peptide fragment $U-V-W$, wherein all amino acid side-chains except for $A_2$ are neutral or protected. In the above peptide fragment formulas X is Prot or Prot-Al, where Prot is a nitrogen protecting group; Y is $A_3$ Q, Ala-$A_3$-Q, $A_3.A_4$-Q, Ala-$A_3$-$A_4$-Q, $A_3$-$A_4$-$A_5$-Q, Ala-$A_3$-$A_4$-$A_5$-Q, Ala-Q or -Q, where: when Y is Q, U is T-$A_3$-$A_4$-$A_5$ or T-Ala-$A_3$-$A_4$-$A_5$; when Y is Ala-Q, U is T-$A_3$-$A_4$-$A_5$; when Y is $A_3$-Q or Ala-$A_3$-Q, U is T-$A_4$-$A_5$; when Y is $A_3$-$A_4$-Q or Ala-$A_3$-$A_4$-Q, U is T-$A_5$; and when Y is $A_3$-$A_4$-$A_5$-Q or Ala-$A_3$-$A_4$-$A_5$-Q, U is T; V is $A_6$ or Z, where: when V is $A_6$, W is $A_7$-Z or Z; when V is Z, W is not present; Al is any naturally occurring L-amino acid, Met(0), DOPA, Abu, or $A_0$-$A'_1$, wherein $A_0$ is H, DOPA, Lys, Phe, Tyr, Cys, Tyr-DAla-Phe-Gly, Tyr-DAla-Gly-Phe, Tyr-Ala-Gly-Thr or Tyr-DAla-Phe-Sar and $A'_1$ is any naturally occurring L-amino acid, Met(O), DOPA or Abu; $A_2$ is His, 3(NMe)His, Ala or Tyr; $A_3$ is a D aromatic amino acid such as DTrp, DPhe, D$^\alpha$Nal, D$^\beta$Nal, N(in)-Me(D/L)Trp, 5-F-(D/L)Trp); $A_4$ is Ala, Gly or Ser; $A_5$ is Trp; $A_6$ is DPhe, D(NMe)Phe or D/L$^\beta$ (Me)Phe; $A_7$ is B-G or G, wherein B is any naturally-occurring amino acid, dipeptides of any naturally-occurring amino acids, $H_2N-(CH_2)n-CO_2H$ and G is Arg, iLys, Lys or Orn, wherein n=2-12, Q is the carboxy terminus of a peptide fragment and is —OH or —M, where M is a moiety capable of being displaced by a nitrogen-containing nucleophile; T represents the amine terminus of the indicated fragment and is H or a protecting group which does not prevent or substantially hinder the coupling reaction; and Z represents the C-terminal end of the polypeptide or peptide fragment, wherein Z is —CONR$^1$R$^2$, —COOR$^1$, —CH$_2$OR$^1$, -Gly-Z', -Met-Z', -Lys-Z', .Cys-Z', -Gly-Tyr Z', or -Ala-Tyr-Z', wherein R$^1$ is H, an alkyl group having from 1 to about 6 carbon atoms, a cycloalkyl group having from 3 to about 8 carbon atoms, an alkenyl group, having from 2 to about 8 carbon atoms or an aryl group having from 6 to about 12 carbon atoms and Z, is —CONR$^1$R$^2$, —COOR$^1$ or —CH$_2$OR$^1$; R$^2$ is defined as R$^1$ and may be the same or different.

Thereafter, one removes the protecting groups. Alternatively, one may use the protected peptide thus formed in further condensations to prepare a larger peptide.

DETAILED DESCRIPTION OF THE INVENTION

A method for synthesizing peptides having biological activity or peptides which are intermediate in forming peptides having biological activity is disclosed. This method comprises condensing the peptide fragment X-A$_2$Y with the peptide fragment U-V-W, wherein X is Prot, or Prot-A$_1$, Y is A$_3$-Q, Ala-A$_3$-Q, A$_3$-A$_4$-Q, Ala-A$_3$-A$_4$-Q, A$_3$-A$_4$-A$_5$-Q, Ala-A$_3$-A$_4$-A$_5$-Q, Ala-Q or Q. When Y is Q, U is T-A$_3$-A$_4$-A$_5$ or T-Ala-A$_3$-A$_4$-A$_5$. When Y is Ala-Q, U is T-A$_3$-A$_4$-A$_5$. When Y is A$_3$-Q or Ala-A$_3$-Q, U is T-A$_4$-A$_5$. When Y is A$_3$-A$_4$-Q or Ala-A$_3$-A$_4$-Q, U is T-A$_5$. When Y is A$_3$-A$_4$-A$_5$-Q or Ala-A$_3$-A$_4$-A$_5$-Q, U is T, V is A$_6$ or Z. When V is A$_6$, W is A$_7$-Z or Z. When V is Z, W is not present.

As used herein an amino acid appearing without a letter preceding it is the "L" form, a "D" signifies the "D" form and "D/L" signifies either form may be present.

A$_1$ is any naturally occurring L-amino acid, Met(O), DOPA, Abu, or A$_0$-A'$_1$.

A$_0$ is H, DOPA, Lys, Phe, Tyr, Cys, Tyr-DAla-Phe-Gly, Tyr-DAla-Gly-Phe, Tyr-Ala-Gly-Thr or Tyr-DAla-Phe-Sar. Preferably, A$_0$ is DOPA, Lys, Phe, and Tyr. A'$_1$ any naturally occurring L-amino acid, Met(O), DOPA or Abu.

A$_1$ or A'$_1$ are preferably any naturally occurring L-amino acid, more preferably A$_1$ or A'$_1$ are Ala or Lys. Most preferably A$_1$ is Ala or Lys.

A$_2$ is His, 3(NMe)His, Ala or Tyr. A$_2$ is preferably His or 3(NMe) His. More preferably A$_2$ is His. The histidine side chain may be either protected (for example, a tosyl protecting group) or unprotected. It is preferred that the histidine side chain is unprotected.

A$_3$ is a D-aromatic amino acid. Preferably, A$_3$ is DTrp, DPhe, D$^\alpha$Nal, D$^\beta$Nal, N-indole-(Me)-D/LTrp, or 5-fluoro-D/LTrp. A$_3$ is more preferably DTrp, D$^\beta$Nal, or DPhe. It is most preferred that A$_3$ is DTrp.

A$_4$ is Ala, Ser, or Gly. A$_4$ is preferably Ala.

A$_5$ is Trp.

A$_6$ is DPhe, D(NMe)Phe, or D/L$^\beta$(Me)Phe. A$_6$ is preferably DPhe or D(NMe)Phe. A$_6$ is most preferably DPhe.

A$_7$ is B-G or G, wherein B is any naturally occurring amino acid, dipeptides of any naturally occurring amino acids. H$_2$N-(CH$_2$)$_n$CO$_2$H (wherein N=2-12) and G is Arg, iLys, Lys or Orn. A$_7$ is preferably B-G wherein B is any naturally occurring amino acid or G. More preferably, A$_7$ is G.

Z represents the carboxy terminal end of the polypeptide or peptide fragment wherein Z is —CONR$^1$R$^2$, —COOR$^1$, —CH$_2$OR$^1$, (wherein R$^1$ is H, an alkyl group having from 1 to about 6 carbon atoms, a cycloalkyl group having from 3 to about 8 carbon atoms, an alkenyl group having from 2 to about 8 carbon atoms, or an aryl group having from 6 to about 12 carbon atoms and R$^2$ is defined as R$^1$ and may be the same or different), -Gly-Z', Met-Z', -Lys-Z',- Cys-Z', -Gly-Tyr-Z', or -Ala-Tyr-Z', wherein Z, is —CONR$^1$R$^2$, —COOR$^1$ or —CH$_2$OR$^1$, wherein R$^1$ and R$^2$ are as defined above. Z is preferably —CONR$^1$R$^2$, —COOR$^1$ or —CO$_2$OR$^1$.

Preferably, A$_7$-Z is G—COOR$^1$, G—CONR$^1$R$^2$ or G—CO$_2$OR$^1$. More preferably, A$_7$-Z is G—CONH$_2$. Most preferably, A$_7$-Z is Lys—NH$_2$.

All amino acid side chains except for A$_2$ are neutral or are protected by a protecting group.

T represents the amine terminus of the indicated fragment and is H or a protecting group which does not prevent or substantially hinder the coupling (i.e., condensation) reaction of the invention. Examples of T moieties include nitrogen protecting groups, for example benzyl. Preferably, T is H.

Prot is a nitrogen protecting group.

Q represents the carboxy terminus of a peptide fragment and is —OH (when Q is OH, in order for Q to be displaced by a nitrogen-containing nucleophile the presence of a dehydrating agent will generally be required) or —M, where M is a moiety capable of being displaced by a nitrogen-containing nucleophile. Such esters and active esters are well known in the art and are also referred to as activating groups. See, for example, the examples described by M. Bodanszky in "Active Esters in Peptide Synthesis", pp. 105–196, *The Peptides*, 1, E. Gross, J. Meienhofer, editors, Academic Press, New York, N.Y., 1981, which is incorporated herein by reference. Q includes compounds (reagents) commonly referred to as mixed and symmetrical anhydrides, which are commonly used in the coupling of amino acids and peptide fragments. Preferably M is an ester or active ester. M can be, for example, —OR$^3$, halogen (i.e., —Cl, —Br, —F, and —I), —SR$^3$ (wherein R$^3$ is an alkyl group containing one to about 10 carbon atoms, an aryl group having from 6 to about 12 carbon atoms, an acyl group of 1 to 12 carbon atoms, or an arylalkyl group having from 7 to about 12 carbon atoms) or a nitrogen-containing cyclic moiety (e.g., a residue of imidazole, succinimide, phthalimide, benzotriazole, a nitro-phenol, N-hydroxy-phthalimide, N-hydroxysuccinimide, N-hydroxy-benzotriazole, etc.). More preferably Q is OH, OR$^3$ or the nitrogen-containing cyclic moiety. R$^3$ is preferably the alkyl group, especially methyl, ethyl or propyl; or the aryl group, especially phenyl and substituted phenyl, for example halogen substituted phenyl. Preferred active esters are electron withdrawing substituents which make good leaving groups for example, N-hydroxy-succinimide, N-hydroxy-phthalimide, and N-hydroxy-benzotriazole. When Q is OH, dehydrating agents (also referred to as coupling agents) will typically be used prior to or during the coupling of X-A$_2$-Y with U-V-W or prior to or during the conversion of OH to an active ester. Preferred dehydrating agents are carbodiimides, in particular dicyclohexylcarbodiimide.

The organic or inorganic pharmaceutically acceptable salts of the starting and/or final peptides or peptide fragments are also contemplated to be within the scope of the invention.

All amino acid side chains except for $A_2$ are neutral or protected. When $A_2$ is His or 3(NMe)His the side chain can be protected but it does not have to be. Neutral side chains can be protected but do not have to be. After the condensation reaction, the protecting groups can be removed. This is generally done when one forms the biologically active peptide. Typically, one would not remove the protecting groups from the peptide intermediate until the penultimate step of preparing the biologically active peptide is complete.

One can also leave protecting groups on the peptide and peptide intermediate if one is not going to use it immediately but store it. For example, the peptide or peptide intermediate can be precipitated, lyophilized or flash frozen for easy storage. The protected peptide intermediate can also be used in further condensations with other peptide fragments or amino acids to produce a larger peptide.

Protecting groups can be removed by conventional deprotecting treatment such as use of acidic reagents, for example, trifluoroacetic acid or hydrochloric acid in the case of, for example, the t-butoxy carbonyl protecting group. In the case of the benzyloxycarbonyl protecting group, hydrogenation is the preferred method of deprotection.

Each of the two peptide fragments is preferably at least 2 amino acid residues. More preferably, one of the two fragments is a tripeptide or tetrapeptide.

The resultant peptide or peptide intermediate formed by this process is at least a tetrapeptide. More preferably, one uses this process to make peptides ranging between 5 and 15 amino acid residues in length. Still more preferably, one uses this method to make peptides ranging from 6 to 11 amino acid residues in length.

The alkyl, alkenyl, aryl, arylalkyl, and aryloxy groups can be substituted or unsubstituted. Preferred substituents include heteroatoms (e.g., O, N, S), halogens (Cl, F, Br, I), hydroxy, alkyl groups containing 1 to about 6 carbon atoms, alkoxy groups, aryloxy groups, nitro groups, etc. More preferred substituents include O, N, hydroxy and alkyl groups.

This method permits the formation of peptides by solution phase methodology without requiring stepwise elongation from the C-terminal amino acid. The stepwise approach is almost exclusively used in solid phase synthesis. Accordingly, this current method permits a greater degree of flexibility in the formation of peptides.

Synthesis of the peptide or peptide intermediate is based upon fragment condensation of peptide fragments. This will typically require fewer steps and thus provide higher overall yield than a stepwise synthesis.

Peptide fragments can be prepared by a variety of means taking standard precautions to minimize problems with racemization such as using racemization inhibitors, the temperature used, etc., which are discussed, infra.

For example, in preparing a peptide fragment, one can start with a commercially available amino acid. However, amino acids can also be prepared by the skilled artisan. Preferably, the amino acid will be protected by one or more protecting groups.

As will be recognized by the skilled artisan from the present disclosure, appropriate use of protecting groups will be desired for the formation of peptide fragments and the chemical coupling of peptide fragments. Thus for acidic (for example, glutamic acid and aspartic acid) and basic side chains (for example ornithine, lysine and arginine) it is generally desirable to use protecting groups which impart the property of neutrality onto the side chains. It is also desirable that the protecting groups utilized for reactive side chains of amino acids be such that the side chains are rendered inert to the conditions of peptide synthesis and fragment coupling. Amino acid side chains which contain hydroxylic (for example threonine or serine) or phenolic (for example tyrosine or DOPA) functionality are often used in either protected or unprotected form depending on the reaction conditions used in the peptide synthesis.

For the fragment coupling of $X-A_2-Y$ and $U-V-W$ of this invention, the skilled artisan will note that the amine terminus of the N-terminal fragment does not participate in the desired bond formation (e.g. X). It is thus desirable that the amine terminus of the N-terminal fragment be protected during fragment coupling. The skilled artisan will also note that the carboxy terminus of the carboxy terminal fragment (e.g. W) also does not participate in the desired bond formation of the fragment coupling. It is thus desirable that the carboxy terminus of the carboxy terminal fragment be protected. Preferably, the carboxy terminus of the C-terminal fragment is protected as a carboxamide as carboxamides are the preferred C-terminus in the peptides prepared by the method of the present invention.

Choice of protecting groups will be determined by a number of factors including inertness to the reaction conditions of synthesis, solubilizing or desolubilizing properties, enhancement of crystallinity, cost, ease of introduction, ease of removal and the like. A large number of protecting groups can be used by those skilled in the art. Examples of such protecting groups are disclosed in The Peptides, vol. 3, "Protection of Functional Groups in Peptide Synthesis", E. Gross and J. Meienhofer eds., 1981, Academic Press, New York, N.Y., which is incorporated herein by reference.

Generally, for amine protection such as Prot, amides and urethanes are preferred protecting groups. Monoacylating protecting groups are preferred. Most preferred are the urethane protecting groups. The most preferred examples of the class of urethane protecting groups include the benzyloxycarbonyl (CBZ) and the t-butoxycarbonyl (Boc) protecting groups. For carboxylic acid groups, ester protection is generally preferred. The most preferred esters are alkyl esters. For the guanidine side chain of arginine it is often not necessary to use protection if highly alkaline reaction conditions can be avoided. The imidazole side chain of histidine can be used in either protected or unprotected form. In a preferred embodiment of this invention, it is preferred that $A_2$ is histidine and it is preferred that $A_2$ be unprotected.

The skilled artisan can make the peptide fragments of the present invention by a variety of ways known in the art based upon the present disclosure. For example, in preparing a fragment, such as U-V-W, one can start with an amino acid amide (which is intended to be the C-terminus of the intended peptide) which is not protected at the alpha-amino nitrogen and contains side chain protection as appropriate. This amino acid amide can be coupled with a N-protected amino acid, or an activated N-protected amino acid such as a N-protected amino acid active ester or a N-protected amino acid imidazolide.

A wide variety of solvents are suited for this solution phase coupling reaction and include but are not limited to such solvents as the protic solvents such as water and alcohols, polar solvents such as dimethylformamide, tetrahydrofuran, or N-methyl-pyrrolidinone and esters such as ethyl acetate, halogenated hydrocarbons such as methylene chloride, as well as nonpolar solvents which include aromatic solvents such as benzene or toluene and saturated or unsaturated hydrocarbons such as heptane. The principal requirements for a solvent in this process will be its solvating power for the amino acids and peptides involved in the reaction, a limited reactivity (relative to the amine component) of the solvent for the activated amino acid residue involved in the coupling reaction, and the ability to permit the coupling reaction to occur with limited to no racemization.

Once a protected peptide intermediate such as $A_6$-$A_7$ has been formed, the nitrogen protecting group can be removed. For example, when the nitrogen protecting group is benzyloxycarbonyl (CBZ), hydrogenolysis in a suitable solvent such as methanol (MeOH) with a catalyst slurry of, for example, 5% Pd/C will effectively remove the nitrogen protecting group. The N-deprotected dipeptide fragment can then be coupled with another amino acid residue as described above to provide a tripeptide fragment. Additional iterations of the above procedure can be used to provide peptide fragments of a larger length.

The above exemplified approach to the synthesis of a peptide fragment proceeds from the C to N terminus of the C-terminal peptide fragment. This approach is particularly suited to the synthesis of C-terminal amide fragments of the present invention. A general scheme showing how to prepare a C-terminal tripeptide amide fragment is set forth below (Scheme 1), although other methods are possible. For example, using different protecting groups or no protecting group.

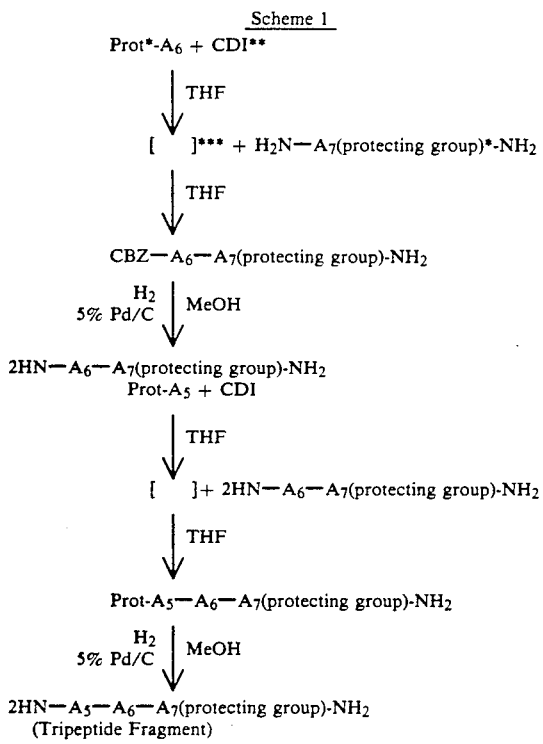

*Protecting groups can be the same or different. The protecting group in parentheses following the amino acid designation is on the side chain of the amino acid.
**CDI = Carbonyldiimidazole
***[  ] = Intermediate This method and the following method (Scheme 2) can readily be adapted by the person of ordinary skill in the art to produce a wide range of peptide fragments of differing lengths.

The N-terminal peptide fragment can also be prepared by a variety of methods. For example, it is often advantageous to prepare the penultimate N-terminal fragment as a peptide ester. When this is the case, it is often advantageous to prepare the N-terminal fragment in a fashion which avoids the intermediacy of an N-deprotected dipeptide ester. In such a fashion diketopiperazine formation can be avoided. One way to avoid the intermediacy of an N-deprotected dipeptide ester is to synthesize the N-terminal fragment of a peptide or peptide intermediate by starting with an amino-acid residue at or near the N-terminus. Thus, in the example set forth in Scheme 2, an N-protected amino acid ($A_2$) is coupled with an N-unprotected amino acid ester ($A_3$). Care must be taken to avoid racemization. Through a judicious choice of N-protecting groups, coupling agent, and reaction conditions and temperature this can be accomplished. Treatment of the resulting N-protected dipeptide ester with a metal hydroxide (preferably sodium or potassium hydroxide) will provide the N-protected dipeptide acid. Care must be taken when using metal hydroxides to minimize the amount of hydroxide and to generally maintain the reaction temperature below 50° C. in order to obtain high yields with minimal racemization. Coupling of the N-protected dipeptide acid with an N-unprotected amino acid ester under conditions which are carefully controlled to minimize racemization provides an N-protected tripeptide ester. Treatment of the N-protected tripeptide ester with a metal hydroxide provides a N-protected tripeptide acid. Alternatively, the same N-protected tripeptide acid can be prepared from the coupling of the N-protected dipeptide acid directly with an unprotected amino acid. This latter approach generally suffers from lower yields.

The amino acid $A_2$ is preferably L-histidine and it is preferable that the imidazole side chain of histidine be unprotected. This unprotected side chain has been found to impart unexpected solubility properties on the peptides intermediates containing $A_2$. Thus, in aqueous solutions, charged peptides are generally found to be soluble in water but zwitterions and neutral molecules are generally found to be insoluble in water. By paying careful attention to the pKa (and pKa's) of the peptide intermediates, it is generally possible to either solubilize the peptides for reaction or to precipitate/crystallize the peptides for the purpose of purification.

Scheme 2 set forth below provides one scheme that can be used for synthesis of an N-terminal tripeptide fragment, although other approaches can be used based upon the present disclosure.

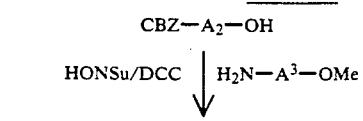

-continued
Scheme 2

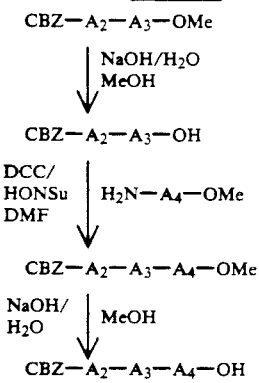

CBZ—A$_2$—A$_3$—OMe

↓ NaOH/H$_2$O, MeOH

CBZ—A$_2$—A$_3$—OH

↓ DCC/HONSu/DMF, H$_2$N—A$_4$—OMe

CBZ—A$_2$—A$_3$—A$_4$—OMe

↓ NaOH/H$_2$O, MeOH

CBZ—A$_2$—A$_3$—A$_4$—OH

The various factors affecting racemization can be taken into account by the skilled artisan to minimize problems with racemization. The nucleophilicity to basicity ratio of the amino component, the solvent used (solvents that enhance separation of charge such as dioxane favor racemization) and the steric hindrance of the amino component, all effect racemization. Thus, the amino acid, the protecting groups, the solvent, the pH and pKa of amino acid side chains will all have an effect.

Additionally, the temperature also effects the degree of racemization. Thus, low temperatures are typically preferred. Preferably, the reaction temperature is as low as possible, but a temperature which will still permit the reaction to occur at an acceptable rate. Preferably, the temperature is between about $-10°$ and about $50°$ C. More preferably, the temperature is between $-10°$ and about $25°$ C., still more preferably, the temperature is between about $0°$ and about $25°$ C. and even more preferably, it is between about $5°$ and about $15°$ C. The above-noted temperature ranges are applicable to both preparation of the starting peptide fragments as well as for the condensation reaction of the invention. The temperature that must be used in a particular reaction can readily be determined empirically based upon the present disclosure.

Still further, one can also use racemization inhibitors. Based upon the present disclosure, racemization at the carboxy terminus of the N-terminal fragment is preferably less than 15%, more preferably less than 10%, still more preferably less than 5%, and most preferably less than 1%.

One of the advantages of the condensation process of the present invention is that peptide products can often (but not necessarily) be purified by precipitation and/or crystallization. Such a purification step tends to remove small amounts of diastereomers which can be formed during racemization at the carboxy terminus prior to coupling.

The products are typically made in a solvent which solubilizes the two fragments such as water or an organic solvent, such as tetrahydrofuran (THF), methanol (MeOH), dimethylformamide (DMF), ethylacetate, toluene, etc. Based upon the present disclosure and the particular constituents, the skilled artisan can readily determine what is the most appropriate solvent to use. Organic solvents are preferred. DMF is most preferred.

The peptide fragments, intermediates and the ultimate peptide can readily be separated from the solution by standard purification techniques, for example, precipitation, in vacuo filtration, crystallization, column chromatography, etc. One unexpected advantage to the present technique is that purifications can generally be accomplished by crystallization or precipitation thereby making the process suitable for large scale production.

The condensation reaction of the two fragments can be accomplished by standard techniques, such as treatment of the two peptide fragments with condensation reagents such as a dehydrating agent (e.g. dicyclohexylcarbodiimide (DCC)) and an activating agent (e.g. N-hydroxysuccinimide (HONSu)) in an organic solvent. In one preferred embodiment, the activating agent is also a racemization inhibitor (e.g. HONSu). Optionally, one may isolate active esters of peptide intermediates, prior to coupling. The resulting protected peptide or protected peptide intermediate is then either used in further peptide synthesis or is then treated by conventional means to remove the protecting groups, for example, by treatment with an acidic reagent such as trifluoroacetic acid in the presence of dimethylsulfide and 1,2-ethanedithiol as carbocation scavengers.

When Q is —OR$^3$ such as —OH, coupling agents commonly know in the art will typically be used to form a peptide bond between the C-terminal peptide fragment and the N-terminal peptide fragment. Such coupling agents include but are not limited to carbonyldiimidazole and carbodiimides such as dicyclohexylcarbodiimide.

When Q is displaced by a nitrogen-containing nucleophile, QH is actually or formally liberated. It is preferred that Q is selected so the resultant QH includes compounds with a pKa under 18. Such compounds include N-hydroxy-succinimide, N-hydroxy-phthalimide, the mono-and di-nitrophenols, halogenated phenols, imidazole, 1-hydroxypiperidine, hydrazoic acid (e.g., N$_3$H, where Q=N$_3$), 1-hydroxybenzotriazole and the like. More preferably, QH represents those compounds for which the Q substituent permits the formation of an amide bond with minimal to no racemization at the amino acid residue bearing the Q substituent, for example, 1-hydroxybenzotriazole and n-hydroxysuccinimide.

Scheme 3 sets forth a general reaction for forming a tetrapeptide fragment from a tripeptide and then a condensation reaction to form a biologically active peptide.

Scheme 3

CBZ—A$_2$—A$_3$—A$_4$—OMe

↓ H$_2$ Pd/C

A$_2$—A$_3$—A$_4$—OMe

↓ Prot-A$_1$(protecting group)-ONSu

Prot-A$_1$(protecting group)-A$_2$—A$_3$—A$_4$—OMe

↓ 1) NaOH  2) HCl

Prot-A$_1$(protecting group)-A$_2$—A$_3$—A$_4$—OH

↓ DCC HONSu, 2HN—A$_5$—A$_6$—A$_7$(protecting group)-NH$_2$

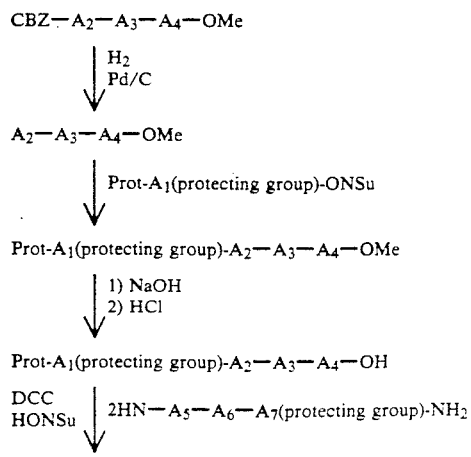

-continued
Scheme 3

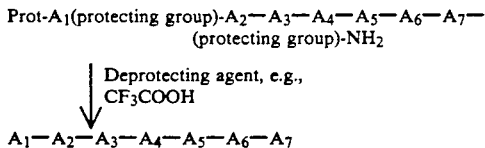

For example, when $A_1$ or $A_7$ is Lys, the protecting group for side chain protection can be Boc. The protecting group for N-terminal protection of the N-terminal fragment can be the appropriate N-terminal protecting group such as Boc or CBZ.

$CF_3COOH$ is useful with acid sensitive protecting groups, The most appropriate deprotecting agent can readily be selected by the skilled artisan based upon the present disclosure and the protecting group used.

Scheme 4 sets forth a general method for forming a peptide intermediate and then forming the resultant biologically active peptide.

Scheme 4

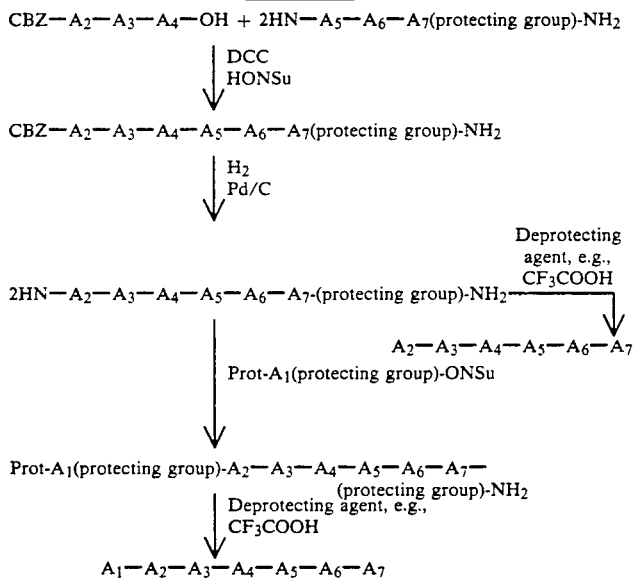

In the above described general method $A_1$ is preferably Ala or Lys (when $A_1$ is Ala, no protecting group is required for the side chain), $A_2$ is preferably His, $A_3$ is preferably DTrp, DPhe, $D^\beta$Nal or $D^\alpha$Nal, $A_4$ is preferably Ala, $A_5$ is preferably Trp, $A_6$ is preferably DPhe and $A_7$ is preferably Lys.

Preferred C-terminal tripeptide fragments include Prot-Trp-DPhe-Lys(Prot)-$NH_2$ (such as CBZ-Trp-DPhe-Lys(Boc)-$NH_2$) and 2HN-Trp-DPhe-Lys(Boc)-$NH_2$ These fragments can be used with a wide variety of other fragments to produce preferred peptides.

For example, when one uses protected fragments such as CBZ-His-DTrp-Ala-Q or Boc-Lys(Boc)-His-$A_3$-Ala-Q (wherein Q is an alkyl ester) such as CBZ-His-DTrp-Ala-OMe, or Boc-Lys(Boc)-His-DTrp-Ala-OMe one can produce CBZ-His-DTrp-Ala—OH or Boc-Lys(Boc)-His-DTrp-Ala—OH, which can be used to produce Lys-His-DTrp-Ala-Trp-DPhe-Lys-$NH_2$ or His-DTrp-Ala-Trp-DPhe-Lys-$NH_2$. Peptide fragments such as CBZ-His-$D^\beta$Nal-Ala-OMe, CBZ-His-$D^\beta$Nal-Ala-OH, CBZ-Ala-His-$D^\beta$Nal-Ala-OMe, CBZ-Ala-His-$D^\beta$Nal-Ala—OH, CBZ-His-$D^\beta$Nal-Ala-OMe, CBZ-His-$D^\beta$Nal-Ala—OH can be used to produce biologically active peptides such as His-$D^\beta$Nal-Ala-Trp-DPhe-Lys-$NH_2$, Ala-His-$D^\beta$Nal-Ala-Trp-DPhe-Lys-$NH_2$ and His-$D^\alpha$Nal-Ala-Trp-DPhe-Lys-$NH_2$. The use of N-benzyloxycarbonyl (CBZ) as a protecting group can simplify purification by producing a product which typically can be crystallized. Other protecting groups can also be used. For example, one typically uses Boc with an amino acid residue such as lysine.

By making appropriate changes to the pH of aqueous solutions it is generally possible to precipitate the fragments, particularly the N-terminal fragment peptide intermediates and peptides from solution. The particular change can be determined empirically by the skilled artisan based upon the present disclosure.

Other peptide fragments than those exemplified above can also be used. For example, when one wants to synthesize a heptapeptide such as Lys-His-DTrp-Ala-Trp-DPhe-Lys-$NH_2$, a variety of different peptide fragments can be used which contrasts to the stepwise synthesis from the C-terminal end. For example, one can use a condensation reaction with a tripeptide as discussed above, such as a protected tripeptide of the formula 2HN-$A_5$-$A_6$-$A_7$(Protected group)-$NH_2$ such as H2N-Trp-DPhe-Lys(Boc)-$NH_2$, and a protected tetrapeptide of the formula Boc-$A_1$-$A_2$-$A_3$-$A_4$—OH such as Boc-Lys(Boc)-His-DTrp-Ala—OH to produce a protected heptapeptide by standard condensation techniques, for example, treatment with dicyclohexylcarbodiimide (DCC) in the presence of N-hydroxysuccinimide (HONSu). The protected heptapeptide is then converted into the desired biologically-active heptapeptide by conventional treatment to remove the protecting group. For example, by treatment with trifluoroacetic acid. Alternatively, one can also use the fragments 2HN-Ala-Trp-DPhe-Lys(Boc)-$NH_2$ and Boc-Lys(Boc)-His-DTrp—OH.

The ultimate biologically active peptide can be made by making a peptide intermediate as discussed above. For example, one can combine two protected peptide fragments, for example, the protected tripeptide CBZ- His-D-Trp-Ala—OH and 2HN-Trp-DPhe-Lys(Boc)-NH₂.

In another embodiment one can use the dipeptide fragment CBZ-His-DTrp—OH with the tetrapeptide fragment 2HN-Ala-Trp-DPhe-Lys(Boc)-NH₂ to produce the peptide intermediate. The resultant protected peptide intermediate can then be used to prepare a biologically-active peptide by a variety of means. For example, the nitrogen protecting group CBZ can be removed by standard means such as methanolic hydrogenolysis to produce the hexapeptide His-DTrp-Ala-Trp-DPhe-Lys(Boc)NH₂. This hexapeptide can then be converted to a desired heptapeptide, for example, by treatment with the N-hydroxysuccinimide ester of Bis-t-butoxycarbonyllysine to produce the protected heptapeptide Boc-Lys(Boc)-His-DTrp-Ala-Trp-DPhe-Lys(-Boc)-NH₂ which can be purified and treated to remove the protecting group. Alternatively, in the above example, the partially deprotected hexapeptide His-DTrp-Ala-Trp-DPhe-Lys(Boc)-NH₂ can be further deprotected by treatment with trifluoroacetic acid to produce a biologically active hexapeptide, His-DTrp-Ala-Trp-DPhe-Lys-NH₂.

In performing the condensation reaction, one uses, for example, DCC and HONSu. The reaction is typically done in an organic solvent, such as dimethylformamide (DMF), at low temperature, such as 5°–10° C. to minimize problems with racemization. Unexpectedly, the resultant protected intermediate can be purified by conventional purification techniques, such as precipitation or crystallization, which would not have been expected to work.

A purified peptide fragment can be added directly to the peptide fragment formed in situ, without having to purify that fragment, for the condensation of the two fragments. This approach can simplify the synthesis process.

The procedure used herein can be performed in a flask, 80 gallon reactor, or industrial scale reactor. The particular fragments one uses depends upon the resultant product and its composition and other concerns. For example, preparing a peptide intermediate which can be used to make a variety of different biologically-active peptides depends upon the particular additional amino acid residue added.

In one preferred form, these processes are used to make polypeptide compounds which promote the release of growth hormone when administered to animals. Some of these peptides have been described, for example, in U.S. Pat. Nos. 4,223,019, 4,223,020, 4,223,021, 4,224,316, 4,226,857, 4,228,155, 4,228,156, 4,228,157, 4,228,158, 4,410,512, 4,410,513, 4,411,890 and 4,839,344. Short-chain polypeptides, which have the ability to promote the release of growth hormone are desirable because they can be easily modified chemically and/or physically and should have excellent transport properties. As a result of the present process, they can be readily and inexpensively prepared as well as easily purified.

The amino acid residue abbreviations used herein are in accordance with the standard peptide nomenclature. Glycine is included in the scope of the term "naturally occurring amino acids". A listing of abbreviations and terms used herein and their respective meanings are as follows:

| | |
|---|---|
| Gly = | Glycine |
| Tyr = | L-Tyrosine |
| Ile = | L-Isoleucine |
| Glu = | L-Glutamic Acid |
| Thr = | L-Threonine |
| Phe = | L-Phenylalanine |
| Ala = | L-Alanine |
| Lys = | L-Lysine |
| Asp = | L-Aspartic Acid |
| Cys = | L-Cysteine |
| Arg = | L-Arginine |
| Gln = | L-Glutamine |
| Pro = | L-Proline |
| Leu = | L-Leucine |
| Met = | L-Methionine |
| Ser = | L-Serine |
| Asn = | L-Asparagine |
| His = | L-Histidine |
| Trp = | L-Tryptophan |
| Val = | L-Valine |
| DOPA = | 3,4-Dihydroxyphenylalanine |
| Met(O) = | Methionine Sulfoxide |
| Abu = | α-Aminobutyric Acid |
| iLys = | $N^\epsilon$-Isopropyl-L-Lysine |
| 4-Abu = | 4-Aminobutyric Acid |
| Orn = | L-Ornithine |
| D$^\alpha$Nal = | α-Naphthyl-D-Alanine |
| D$^\beta$Nal = | β-Naphthyl-D-Alanine |
| Sar = | Sarcosine |
| DMF = | Dimethylformamide |
| CBZ = | Benzyloxycarbonyl |
| Boc = | t-Butoxycarbonyl |
| Me = | Methyl |
| THF = | Tetrahydrofuran |
| CDI = | Carbonyldiimidazole |
| Pd/C = | Palladium on Carbon |
| DCC = | Dicyclohexylcarbodiimide |
| HONSu = | N-Eydroxysuccinimide |
| 3(NMe)His = | Histidine wherein the imidazole nitrogen on the three position is methylated |
| N(in)Me(D/L)Trp = | D/L Tryptophan wherein the indole nitrogen is methylated |
| 5-F-(D/LTrp) = | D/L Tryptophan wherein the 5-position is fluorinated |
| D(NMe)Phe = | D-Phenylalanine wherein the α nitrogen is methylated |
| D/L$^\beta$(Me)Phe = | D/L Phenylalanine wherein the β-carbon is methylated |

Pharmaceutically acceptable salts of these peptides can be used and are preferred when administration to human subjects is contemplated. Such salts include the non-toxic alkali metal, alkaline earth metal and ammonium salts commonly used in the pharmaceutical industry, including sodium, potassium, lithium, calcium, magnesium, barium, ammonium, and protamine salts, which are prepared by methods well known in the art. The term also includes non-toxic acid addition salts which are generally prepared by reacting the resultant compounds with a suitable organic or inorganic acid. Representative salts include hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napthylate and the like.

This invention will be further illustrated by the examples that follow. These examples are provided to aid in the understanding of the invention and are not to be construed as a limitation thereof.

EXAMPLES

General Procedures

Melting points were determined using a Thomas Hoover capillary melting point apparatus and are uncorrected. Infrared (IR) spectra were recorded on a Perkin-Elmer Model 137 or a Nicolet Model 5DX spectrophotometer and are reported in wave numbers (cm$^{-1}$). All mass spectra (MS) were obtained using a VG Analytical Ltd. Model ZAB-1F Mass Spectrometer in EI (electron impact), FD (field desorption) or FAB (fast atom bombardment) modes. GCMS were obtained using a Finnigan 4023 GCMS equipped with a 30 m DB5 capillary column (J & W Scientific) using helium carrier gas. Elemental analyses were performed by Eastman Chemical Division's Physical and Analytical Chemistry Research Division. Optical rotations were measured using an Autopol III polarimeter manufactured by Rudolph Research.

Unless otherwise specified, all $^1$H NMR spectra were obtained on a JEOL GX-400 NMR instrument operating at 400 MHz or a JEOL GX-270 NMR instrument operating at 270 MHz. These instruments are capable of a routine digital resolution of less than 0.7 Hz. Chemical shifts are expressed in parts per million relative to internal 3-(trimethylsilyl) tetradeutero sodium propionate (TSP).

High performance liquid chromatography (HPLC) was accomplished using a Hitachi system consisting of a L-5000 gradient controller and a 655A pump attached to a Vydac 201TP1010 or 218TP1010 semipreparative column. Combinations of water containing 0.2% trifluoroacetic acid and methanol were used as the eluting solvent. Typically, compounds of interest were eluted at a flow rate of six mL per minute with a gradient increasing the organic component at a rate of approximately 1-2% per minute. Compounds were detected at appropriate wavelengths using an LKB 2140 diode array U.V. detector. Integrations were accomplished using Nelson Analytical software (Version 3.6).

All reactions were carried out under an inert atmosphere of nitrogen or argon unless otherwise specified. Anhydrous tetrahydrofuran (THF, U.V. grade) and dimethylformamide (DMF) were purchased from Burdick and Jackson and used directly from the bottle.

A(a). Preparation of Tripeptide Fragment—$_2$HN-Trp-DPhe-Lys(Boc)-NH$_2$

N$^\alpha$-Benzyloxycarbonyl-(N$^\epsilon$-t-butoxycarbonyl)lysine Amide 4

To a 10° C. solution of carbonyldiimidazole (CDI, 2, 88.24 g, 0.544 mol) and dry tetrahydrofuran (THF, 1500 mL), N$^\alpha$-benzyloxycarbonyl-(N$^\epsilon$-t-butoxycarbonyl)lysine (1, 180 g, 0.474 mol), was slowly added. Gas evolution was observed during this addition. While the N$^\alpha$-benzyloxycarbonyl-(N$^\epsilon$-t-butoxycarbonyl)lysine imidazolide intermediate, 3, was forming, a saturated solution of ammonia and THF (2000 mL) was prepared (anhyd. NH$_3$ gas was passed through THF at 5°-10° C). After formation of intermediate 3 was judged to be complete (when gas evolution had ceased, approximately 2 hours), one-half of the THF solution containing 3 was added to the ammonia solution. The remainder of the solution containing 3 was added 30 minutes later. A continuous flow of ammonia gas was maintained throughout the additions and for an additional 45 minutes thereafter. Upon addition of the two solutions containing 3, a white precipitate formed. The reaction was allowed to warm to room temperature and to stir for 15 hours. Solvent was removed from the slurry in vacuo. The residue was slurried in water, and the resulting solid was collected by vacuum filtration. Analyses by $^1$H NMR and FDMS were consistent with the presence of 4 at a high level of purity (181.48 g, 0.479 mol, 101% with trace amounts of solvent present).

N$^\epsilon$-t-Butoxycarbonyl-lysine-amide, 5

A solution of the lysine amide 4 (181.48 g, 0.479 mol) in methanol (MeOH, 1000 mL) was added to a catalyst slurry of 5% Pd/C (5g) in methanol (250 mL) under argon. Hydrogen was bubbled through the reaction mixture (ca. 15 minutes) and the reaction was then stirred under an atmosphere of hydrogen until HPLC analysis indicated that the reaction was complete (36 hours). The hydrogen atmosphere was then displaced with argon. The reaction solution was clarified through a Celite® pad and solvent was removed in vacuo to provide a solid. Analysis by $^1$H NMR and FDMS indicated that the isolated material was consistent with the amine 5 (110.75 g, 0.452 mol, 94%).

N$^\alpha$-Benzyloxycarbonyl-D-phenylalanyl-(N$^\epsilon$-t-butoxycarbonyl) Lysine-amide, 8

N$^\alpha$-Benzyloxycarbonyl-D-phenylalanine (6, 126.39 g, 0.423 mol) was slowly added to a 10° C. solution of CDI (2, 66.03 g, 0.409 mol) in THF (500 mL). Gas evolution was observed during the addition. When gas evolution ceased, the lysine amide 5 (110.75 g, 0.452 mol) was added as a solution in THF (500 mL). After approximately 48 hours the mixture was filtered to remove solids. The filtrate was concentrated in vacuo.

The resulting residue was taken up in ethyl acetate (EtOAc, 500 mL) and washed as follows in a separatory funnel:

1. aqueous HCl (1N, 3×500 mL) pH of wash 1 was 8; subsequent wash pH's, about 1.
2. water (500 mL)
3. aqueous Na$_2$CO$_3$(½ saturated, 2×500 mL), filtered to collect the formed crystalline solids (142.77 g, 0.271 mol, 66%).
4. Water (3×500 mL).

The organic layer was dried over MgSO$_4$. After clarification, the solvent was removed in vacuo. The resulting residue was recrystallized from hot EtOAc to provide a second sample of 8 (30 g, 0.057 mol, ca. 14%). Analyses of both crops of crystalline solids by $^1$H NMR and FDMS were consistent with 8. This reaction afforded an approximate 80% combined product yield.

D-Phenylalanyl-(N$^\epsilon$-t-butoxycarbonyl)lysine-amide, 9

A methanolic solution (1500 mL) of amide 8 (120.53 g, 0.229 mol) was added to a catalyst slurry of 5% Pd/C (50 g) in MeOH (200 mL). The argon atmosphere was displaced with hydrogen. When HPLC analysis indicated that the reaction was complete (4 hours), the hydrogen atmosphere was displaced with argon. The reaction solution was then clarified through a Celite® pad and the filtrate was taken to a residue in vacuo. This reaction afforded a 68% yield of dipeptide 9 (60.75 g, 0.155 mol). This dipeptide product was used directly in the preparation of tripeptide 12. Due to the high purity of the hydrogenation product as determined by $^1$H NMR analysis, the low overall yield is believed to be due to a poor solubility of the product or an adherence of the product to the Pd/C catalyst which was removed by filtration

N$^\alpha$-Benzyloxycarbonyl-tryptophyl-D-phenylalanyl-(N$^\epsilon$-t-butoxycarbonyl)lysine-amide, 12

A 10° C. solution of N$^\alpha$-benzyloxycarbonyl-tryptophan (10, 67.60 g, 0.200 mol), THF (500 mL), and CDI (2, 33.05 g, 0.204 mol) was stirred until gas evolution had ceased. A solution of 9 (40.8 g, 0.103 mol) in THF (ca. 200 mL) was added to the reaction mixture. The resulting solution was allowed to react for 15 hours while warming to room temperature. The solid which had formed was then collected by vacuum filtration. The filtrate was taken to a residue by concentration in vacuo. The resulting residue and solid were recombined and taken up in EtOAc (4000 mL) with slight warming. Upon cooling the solution to room temperature, a solid formed. The solid (34.53 g) was collected by vacuum filtration. This solid was recrystallized from hot MeOH to afford the purified tripeptide 12 (22.36 g, 0.031 mol). The EtOAc filtrate (from the first crystallization) was washed as follows in a separatory funnel:

1. aqueous HCl (1 N, 2×500 mL)
2. water (1×500 mL)
3. aqueous Na$_2$CO$_3$ (½ saturated, 2×500 mL)
4. aqueous NaCl (1×500 mL)

The organic layer was dried over MgSO$_4$ and then clarified by vacuum filtration. The solvent of the filtrate was removed in vacuo. The resulting residue was taken up in EtOAc as before to afford a dry solid (22.53 g). The solid was subjected to a hot MeOH recrystallization to afford a second crop of 12 as a white solid (15.04 g, 0.021 mol). This reaction was afforded an overall 51% yield of purified product (37.40 g, 0.053 mol). The $^1$H NMR and FDMS data obtained on this product were consistent with the tripeptide 12. A scale up of this procedure (ca. 0.15 mole scale) was performed with an overall 60% product yield.

Tryptophyl-D-phenylalanyl-(N$^\epsilon$-t-butyloxycarbonyl)lysine-amide 13

A methanolic solution (1500 mL) of tripeptide 12 (64.59 g, 0.091 mol) was added to a catalyst slurry of 5% Pd/C (5 g) and MeOH (250 mL) under an argon atmosphere. An additional volume of MeOH (2250 mL) was added. The argon atmosphere was displaced with hydrogen and allowed to react (24 hours). Upon completion of the reaction (the disappearance of the starting peptide was established by HPLC), the hydrogen atmosphere was displaced with argon. The solution was clarified through a Celite®, pad and the filtrate was concentrated in vacuo to provide tripeptide 13 (50.31 g, 0.087 mol, 96%) as a white solid. The $^1$H NMR and FDMS data obtained from this solid were consistent with tripeptide 13. This material was used directly in the preparations of the peptide and of the peptide intermediate.

A(b). The Following Compounds (17 and 21) Represent Examples Which Provide an Undesirable By-product (21)

To a 10° solution of dry THF (500 mL) and 2 (26.36 g, 0.163 mol), N$^\alpha$-benzyloxycarbonyl-D-tryptophan (14, 50.0 g, 0.148 mol) was added and allowed to react to form the intermediate N$^\alpha$-benzyloxycarbonyl-D-tryptophan imidazolide. The resulting solution was allowed to stir until the evolution of gas had ceased. Alanine methyl ester hydrochloride (15, 24.85 g, 0.178 mol) and N-methylmorpholine (16, 17.95 g, 0.178 mol) were added to the resulting solution. The reaction was monitored by HPLC. Upon completion of the coupling, the solids which had formed during the reaction were collected by vacuum filtration. The filtrate was concentrated under reduced pressure to yield an oil which slowly crystallized. Both the solid and oil were analyzed by HPLC. The results indicated that dipeptide 17 was present in both samples. The partially crystallized oil and solid were combined and triturated with EtOAc. The resulting crystalline mass was collected by vacuum filtration. The filtrate was saved. The crystalline mass was slurried into EtOAc (1000 mL) and was washed as follows:

1. 1N HCL (2×500 mL)
2. water (1×500 mL),
3. Na$_2$CO$_3$ (½ saturated, 2×500 mL),
4. water (1×500 mL)

The solid in the organic phase was collected by vacuum filtration (6.30 g, 0.015 mol, 11%). Proton NMR indicated this solid sample of 17 to be of high purity.

Cyclo-D-tryptophyl-L-alanine, 21

A solution of dipeptide 17 (27.00 g, 0.064 mol) in MeOH (2500 mL) was cautiously added to a round bottom flask containing 5% Pd/C (20 g) under an argon atmosphere. The system was purged with argon and then hydrogen was continuously bubbled through the reaction solution. Small aliquots (ca. 25 mL.) were removed from the reaction mixture and the hydrogenation was monitored by $^1$H NMR (60 MHz). Concurrent with the execution of the above reaction, the intermediate N$^\alpha$-benzyloxycarbonyl-histidine imidazolide 19a was formed by combining dry THF (500 mL), 2 (13.64 g, 0.084 mol), and N$^\alpha$-benzyloxycarbonyl-histidine (19, 23.99 g 0.083 mol) under an argon atmosphere. The mixture was stirred at 0°–10° C., but did not form a solution. The mixture was allowed to warm to room temperature which resulted in a partial solution. The resulting suspension was allowed to stir until evolution of gas had ceased. At the end of 1 hour, the hydrogenation of dipeptide 17 was complete ($^1$H NMR). The hydrogenation mixture was purged with argon and then clarified by passing it through a Celite® pad. The clarified solution was concentrated to a residue under reduced pressure. The resulting residue was taken up in dry DMF and was added to the solution-suspension which was presumed to contain 19a. The resulting suspension was allowed to stir at room temperature for ca. 17 hours. Solids had formed during the reaction; water was added, forming a solution. The solution tested ninhydrin positive. The solution was taken to a residue by concentration in vacuo to yield a yellow-brown oil. A dilute solution of Na$_2$CO$_3$ (pH 8) was added to precipitate product. The resulting solid was collected by vacuum filtration and the filtrate was lyopholized. The solid was slurried in water and collected by filtration. The collected solid was dried under reduced pressure and the aqueous filtrate was lyopholized. $^1$H NMR and FDMS data on all isolated materials indicated that N$^\alpha$-benzyloxycarbonyl-histidyl-D-tryptophyl-alanine methyl ester (20) had not been prepared but that the diketopiperazine 21 had instead been formed and was in fact present at a high level of purity in the solid (7.95 g, 0.031 mol, 49%).

B. Preparation of Tripeptide Fragment-CBZ-His-DTrp-Ala-OMe, N$^\alpha$-Benzyloxycarbonyl-D-tryptophyl-alanine Methyl Ester, 17

N$^\alpha$-Benzyloxycarbonyl-histidyl-D-tryptophan Methyl Ester, 25

A solution of EtOAc (400 mL) and D-tryptophan methyl ester hydrochloride (22, 158 g, 0.62 mol) was washed with saturated sodium carbonate (400 mL) and 0.8 N aqueous sodium hydroxide (ca. 500 mL). The resulting aqueous phase was removed (pH 8.5) and the organic phase was sequentially washed with half-saturated aqueous Na$_2$CO$_3$ (150 mL) and then with water (50 mL). The free base form of 22 was isolated upon concentration of the ethyl acetate layer in vacuo (115.6, 0.53 mol, 85%). Higher yields of the free base of tryptophan methyl ester seem to have been obtained when the pH of the first aqueous wash was adjusted to ca. 10.

Dicyclohexylcarbodiimide (DCC, ca. 95 g, 0.46 mol) was added to a $-5°$ C. (ice-ethanol bath) solution of N$^\alpha$-benzyloxycarbonyl-histidine (19, 143.5 g, 0.50 mol), N-hydroxysuccinimide (HOSU, 23, 77.5 g, 0.62 mol) and the freshly prepared free base form of 22 (114.5 g, ca. 0.52 mol) in DMF (ca. 3L). The resulting reaction solution was allowed to stir for 24 hours while warming to room temperature. HPLC analysis at this point showed the reaction to be incomplete. The reaction solution was then cooled to ca. $-5°$ C. and an additional portion of dicyclohexylcarbodiimide (ca. 35 g, ca. 0.17 mol) was added to the reaction. The reaction mixture was then allowed to stir for an additional 24 hours while warming to room temperature. The mixture was then filtered to remove dicyclohexylurea (DCU). Water (1 L) was added to the filtrate and the resulting solution was concentrated in vacuo. The resulting residue was taken up in aqueous 1N HCl (ca. 1 L until the pH of the aqueous phase reached a pH of 1). The aqueous phase was then extracted with two portions of ethyl acetate (1 L each). The pH of the aqueous phase was then adjusted by addition of cold 2N sodium hydroxide (500 mL) and sodium hydroxide pellets. During this neutralization, the solution was kept cold by addition of cold ethyl acetate (1 L). When the pH of the aqueous phase had reached 7, copious precipitation of a white solid resulted. This solid was collected by vacuum filtration and washed sequentially with half saturated sodium carbonate (2×1500 mL), water (6×1500 mL) and ethyl acetate (3×1500 mL). The resulting filter cake was dried under high vacuum to constant weight. The $^1$H NMR spectrum of this material (187.1 g, ca. 0.38 mol, ca. 77%) was consistent with a product containing 25 as a single isomer in the presence of small amounts of dicyclohexylurea. This material was hydrolyzed directly without further purification.

N$^\alpha$-Benzyloxycarbonyl-histidyl-D-tryptophan, 26

Aqueous sodium hydroxide (15.4 g, 192 mL, 0.08 g/mL solution, 0.38 mol) was added to a solution of dipeptide 25 (187.1 g, ca. 0.38 mol), water (360 mL) and MeOH (ca. 6 L). The solution was stirred at room temperature until hydrolysis was complete (ca. 24 hours). The disappearance of the starting peptide was established by HPLC analysis. The solution was concentrated in vacuo to a residue which was dissolved in water (ca. 1 L). The aqueous layer (pH ca. 10) was then extracted with EtOAc (2×500 mL) in a separatory funnel. The resulting aqueous phase was adjusted to a pH of 5 with concentrated HCl at which point a crystalline precipitate formed. The solid was collected by vacuum filtration and dried in vacuo (148.4 g, 0.31 mol, 82%). The pH of the filtrate was adjusted to 4.5. A second crop of solid was again collected by vacuum filtration and dried in vacuo (20.2 g, 0.043 mol, 11%). $^1$H NMR showed both samples to contain dipeptide 26 in high purity. In two repetitions of this reaction, yields of 83% (ca. 0.06 mole scale) and 58% (ca. 0.3 mole scale) were obtained.

N$^\alpha$-Benzyloxycarbonyl-histidyl-D-tryptophyl-alanine Methyl Ester, 20

The dipeptide N$^\alpha$-benzyloxycarbonyl-histidyl-D-tryptophan (26, 120 g, 0.253 mol) was added to a solution of the HONSu (23, 58.10 g 0.505 mol) in DMF (800 mL) under an atmosphere of argon. To this solution, a mixture of alanine methyl ester hydrochloride (15, 42.29 g 0.303 mol), N-methylmorpholine (16, 30.66 g, 0.303 mol) and DMF (200 mL) was added. The resulting solution was cooled to 10° C., at which time dicyclohexylcarbodiimide (24, 54.64 g, 0.265 mol) in methylene chloride (273 mL) was added. The reaction was monitored by HPLC while the reaction temperature was maintained at 10° C. After 4 days, the reaction had not progressed to completion. An additional charge of 24 (16.4 g, 0.080 mol) was added and the reaction mixture was allowed to stir for an additional day at 10° C. After this period of time, HPLC analysis indicated that the reaction had gone to completion. The solids which had formed during the reaction were collected by vacuum filtration. The filtrate was then concentrated to a residue in vacuo. The resulting residue was taken up in ethyl acetate (ca. 500 mL) and extracted with half-saturated aqueous Na$_2$CO$_3$ (2×500 mL). The ethyl acetate phase was dried over MgSO$_4$. The resulting solution was clarified and concentrated to a residue in vacuo. During concentration of this solution, a solid formed. This solid was collected and the solution was concentrated to a viscous oil in vacuo which was consistent with 20 (151.5 g, solvent wet, ca. 100%) by $^1$H NMR and FDMS. The solids which were isolated during the final concentration proved to be impurities upon analysis by FDMS, (base peak of 449, no molecular ion showing for product). The viscous oil containing tripeptide 20 was not further purified but was used directly in the preparation of peptide fragments.

C. Preparation of Tetrapeptide Fragment-Boc-Lys(Boc)-His-DTrp-Ala-OH

Histidyl-D-Tryptophyl-Alanine Methyl Ester, 30

Five percent palladium on carbon (3 g) was carefully added to a solution of N$^\alpha$-benzyloxycarbonyl-histidyl-D-tryptophyl-alanine methyl ester 20 (40.1 g, 71 mmol) in methanol (500 mL) under an argon atmosphere. Argon was bubbled through the reaction mixture for 15 minutes and acetic acid (15 mL, 0.26 mol) was then added. Hydrogen was bubbled (subsurface) through the resulting mixture for 15 minutes and then the reaction was allowed to stir at room temperature under a hydrogen ballast (1 atm). After a total of five days, HPLC analysis indicated that approximately 10% of the starting material remained. After carefully bubbling argon through the reaction mixture (subsurface for 30 minutes), an additional portion of 5% palladium on carbon (2.5 g) was added. On the following day, for a total of six days of reaction, argon was once again bubbled through the reaction mixture and the resulting solution was clarified by filtration through a pad of diatomaceous earth. The resulting solution was concentrated in vacuo to provide a solid foam (39.40 g) which appeared to contain three equivalents of acetic acid by $^1$H NMR in addition to the desired product. A portion of this foam (31.88 g) was dissolved in water (500 mL) and filtered to remove a small amount of particulates (determined to be dicyclohexylurea by $^1$H NMR which had presumably been carried through from previous reactions). Ethyl acetate (500 mL) and saturated aqueous sodium carbonate were added to the resulting filtrate. Vigorous mixing of the layers resulted in the formation of a solid suspension which was filtered. The resulting filter cake was washed with ethyl acetate (300 mL) and water (3×200 mL). The now white solid was dried to constant weight in vacuo to provide His-D-Trp-Ala-OMe (30) (8.71, 20.4 mmol, 35%).

FDMS=427 (M+1)

Bis-Boc-Lysine N-hydroxysuccinimide Ester, 31

Dicyclohexylcarbodiimide (8.9 g, 43 mmol) was added to a room temperature solution of (Boc)$_2$lysine (15 g, 43 mmol) and N-hydroxysuccinimide (5.48 g, 48 mmol) in methylene chloride (250 mL). The resulting solution was allowed to stir overnight. The reaction mixture was then filtered to remove dicyclohexylurea and the clarified filtrate was concentrated in vacuo to a white solid (19.0 g, ca. 42 mmol, ca. 97%) which was shown to contain 31 as the predominate product by $^1$H NMR and FDMS (M+ =443). Ester 31 was stored at −20° C. under an argon atmosphere prior to use. Repeating the above procedure but with prolonged drying in vacuo produced a foam rather than an oil.

Boc-Lys(Boc)-His-D-Trp-Ala-OMe, 32

N$^\alpha$, N$^\epsilon$-bis-t-butoxycarbonyl-lysine-N-hydroxysuccinimide ester [10.6 g, 23.9 mmol]was added to a solution of His-D-Trp-Ala-OMe (30) (8.58 g, 20.1 mmol) in anhydrous dimethylformamide (DMF, 200 mL). The resulting homogeneous solution was allowed to stir over the weekend at room temperature. After a total of three days, HPLC analysis indicated that less that 1% of the tripeptide remained in the reaction mixture. Water (50 mL) was added to the reaction and the resulting mixture was allowed to stir for an additional day. This solution was then concentrated in vacuo. The resulting oily residue was dissolved in ethyl acetate (500 mL) and extracted with half-saturated aqueous sodium carbonate (2×300 mL). The organic phase was dried by filtration through MgSO$_4$ and Na$_2$SO$_4$ and concentrated in vacuo to provide the tetrapeptide as a solid foam (15.74 g, 20.9 mmol, 104%). This material was used without further purification in the preparation of Boc-Lys(Boc)-His-D-Trp-Ala-OH.

FDMS=755 (M+1)

Boc-Lys(Boc)-His-D-Trp-Ala-OH, 33

A 2N aqueous sodium hydroxide solution (7.5 mL, 15 mmol) was added to a methanol (500 mL) and water solution (200 mL) containing Boc-Lys(Boc)-His-D-Trp-Ala-OMe (10.35 g, 13.7 mmol). After the reaction was allowed to stir overnight at room temperature, HPLC analysis indicated that less than 3% of the starting material remained. The resulting solution was concentrated in vacuo to a volume of approximately 200 mL. Water (100 mL) was added and the pH was adjusted to approximately 12 by addition of 2N sodium hydroxide (1 mL). The resulting solution was extracted with ethyl acetate (2×500 mL). The pH of the aqueous phase was then adjusted to 5 by addition of aqueous HCl which resulted in the precipitation of an oil. The aqueous phase was decanted away from the oil and the oil was then rinsed with water (2×50 mL). This oil was converted to a solid foam upon drying to constant weight in vacuo (5.62 g, 55%). $^1$H NMR indicated the presence of a single isomer in high purity.

FDMS=741 (M+1)

D. Condensation Reaction of Peptide Fragments to Produce Heptapeptide
Boc-Lys(Boc)-His-D-Trp-Ala-Trp-D-Phe-Lys(Boc)-NH$_2$, 34

The two peptides Boc-Lys(Boc)-His-DTrp-Ala-OH (33, 1.91 g, 2.6 mmol) and Trp-DPhe-Lys(Boc)-NH$_2$ (13, 1.64 g, 2.8 mmol) were dissolved in anhydrous DMF and the resulting solution was concentrated in vacuo to produce a viscous oil. This preliminary concentration was carried out in an attempt to remove traces of methanol which had been observed in the $^1$H NMR of both peptide samples. The resultant peptide mixture was redissolved in DMF (200 ml) and N-hydroxysuccinimide (0.59 g, 5.1 mmol) was then added. The resulting solution was then cooled to a solution temperature of −2° C. and dicyclohexylcarbodiimide (0.7 g, 3.4 mmol) was then added as a solution in methylene chloride (3.5 mL). The resulting reaction mixture was allowed to stir at −2° C. solution temperature for a period of three days. After this period of time, HPLC analysis indicated that less than 50% of the starting materials had reacted. Additional dicyclohexylcarbodiimide (0.8 g, 3.9 mmol in 4 mL of methylene chloride) was then added and the resultant reaction mixture was allowed to stir for an additional day at −2° C. On the following day (for a total of four days) when HPLC analysis again indicated incomplete reaction, cooling of the reaction mixture was terminated. Over a period of eight hours the solution temperature of the reaction rose to 18° C. The resultant reaction mixture was allowed to stir overnight at room temperature. On the following morning HPLC analysis indicated that less than 2% of the tetrapeptide, Boc-Lys(Boc)-His-D-Trp-Ala-OH (33), remained (as judged by the relative intensities of absorptions at 280 nm). Water (50 mL) was added and the resulting mixture was allowed to stir for an additional day. The reaction solution was then filtered to remove dicyclohexylurea and the resulting filtrate was concentrated in vacuo to a viscous oil. Ethyl acetate (250 mL) and half-saturated aqueous sodium carbonate (200 mL) were added to the resulting residue. The two-phase mixture was vigorously swirled on a rotary evaporator for approximately one hour to cause precipitation of a gelatinous solid. The solids were collected by filtration on a scintered glass funnel. The resultant solids were washed with water (2×200 mL) and ethyl acetate (200 mL) and dried to constant weight in vacuo (34, 1.67 g, 50%). A second, more impure crop of peptide 34 was obtained by combining all of the filtrates from the above isolation procedure and isolating the ethyl acetate phase. Concentration of the ethyl acetate solution provided the second impure crop of 34 which was suspended in water and lyophilized (1.56 g). This second crop was not used or further purified. $^1$H NMR analysis of this second crop indicated that the major component in this material was 34.

FDMS=1301 (M+1)

Lys-His-D-Trp-Ala-Trp-D-Phe-Lys-NH₂, 35

The heptapeptide Boc-Lys(Boc)-His-D-Trp-Ala-Trp-D-Phe-Lys-(Boc)-NH₂ (34, 1.33 g, 1.02 mmol) was added to a room temperature solution of trifluoroacetic acid (30 mL), dimethylsulfide (14 mL), 1,2 ethanedithiol (7 mL) and anisole (2.2 mL) in methylene chloride (15 mL). The homogeneous reaction mixture was allowed to stir for 15 minutes. After this period of time, anhydrous ether (450 mL) was added to cause precipitation of the crude biologically active peptide product 35. This product was isolated by filtration on a scintered glass funnel. The resultant apparently nonhygroscopic product was dissolved in water and lyophilized. Upon completion of lyophilization there was produced a fluffy white solid (1.46 g) which was shown to consist of two products by HPLC in a ratio of approximately three to one. The major, more rapidly eluting product was established to be 35 by coelution on HPLC with an authentic sample. The crude peptide product was purified by medium pressure chromatography on a 26×460 mm glass column containing Lichroprep TM RP-18 column packing material (C-18, 25–40 nm, irregular mesh). After injection of the peptide as a solution in water, the column was eluted at a flow rate of 9 mL per minute with a shallow gradient of 10 to 25% methanol over 5 hours, followed by a gradient of 25 to 35% methanol over 6.7 hours. The concentration of methanol was then held constant at 35% for 6 hours. The methanol concentration of the gradient was then increased at a rate of 1% per hour. During the elution, the remainder of the solvent composition was made up of water containing 0.2% trifluoroacetic acid. The product (35) (0.76 g, 0.53 mmol, 51% after lyophilization) was isolated from that portion of the gradient in which the methanol concentration ranged from 32% to 36% (ca. 1 gallon of solution). High resolution proton NMR data obtained on a sample prepared by this method was essentially identical and super-imposable with high resolution proton NMR data obtained on a purified sample of 35 prepared by the methodology described infra. The second slower eluting impurity (0.13 g) was eluted in later fractions at a methanol concentration of approximately 46%. A mixed fraction containing both 35 and the later eluting component was also obtained (0.14 g).

FDMS (35) = 1001 (M+1)

FDMS (slower eluting impurity) = 1101. The molecular weight of 1101 for this slower eluting impurity, strongly suggests the presence of a single t-butoxy carbonyl group. A single t-butoxy carbonyl peak was observed for this impurity (contaminated with 35) in the ¹H NMR. It follows that treatment of (Boc)₂-Lys-His-D-Trp-Ala-Trp-D-Phe-Lys(Boc)-NH₂ for a longer period of time with triflouroacetic acid would significantly increase both the crude product purity and yield of 35.

Analysis: Calc for $C_{52}H_{68}N_{14}O_7 \cdot 4TFA$: C,49.45; H, 4.98; N,13.46; F, 15.64
Found: C,47.5; H,4.78; N,12.14; F,16.15 (for 35)
Calc for $C_{52}H_{68}N_{14}O_7 \cdot 5TFA$: C,47.39; H,4.64; N,12.48; F,18.14.

E. Synthesis of Hexapeptide Intermediate

Nα-Benzyloxycarbonyl-histidyl-D-tryptophyl-alanine, 27

Under an argon atmosphere, the viscous oil containing tripeptide 20 (ca. 0.253 mol), was hydrolyzed in a solution of MeOH (1500 mL), H20 (500 mL) and NaOH (0.08 g/mL, 11.11 g, 0.278 mol). The reaction was allowed to react at room temperature (ca. 25° C.) while being monitored by HPLC. After two days, HPLC analysis indicated that hydrolysis was complete. The solution was concentrated to a residue in vacuo. Water (500 mL) was then added to the residue. The pH of the resulting solution was ca. 10. This aqueous solution was then extracted with EtOAc (2×500 mL). After this extraction the pH of the aqueous layer was ca. 9. All insoluble material in the aqueous layer was collected by vacuum filtration. The pH of the filtrate was then adjusted to ca. 5 with 2N HCl. This resulted in the precipitation of an oil which was isolated from the aqueous layer by decantation. The oil was taken up in a methanol-water solution and concentrated to a residue in vacuo (109.42 g, 0.200 mol, ca. 79% overall yield from dipeptide 26). This isolated material was consistent with 27 by ¹H NMR FDMS=547, M+1.

Nα-Benzyloxycarbonyl-histidyl-D-tryptophyl-alanyl-tryptophyl-D-phenylalanyl-(-Nε-t-butyloxycarbonyl)lysine Amide, 28

Dicyclohexylcarbodiimide (24, 2.49 g, 0.0121 mol) in methylene chloride (12.5 mL) was added to a 0° C. solution of 13 (6.99 g, 0.0121 mol), 27 (6.00 g, 0.0110 mol), and 23 (2.53 g, 0.0220 mol) in DMF (100 mL). The reaction was monitored by HPLC. After 6 days, the reaction was complete. The reaction was filtered to remove dicyclohexylurea. Water was added and the resulting solution was concentrated in vacuo. The resulting oil was taken up in EtOAc resulting in the formation of a solid. After setting for one hour, the solid reverted to an oil. This material was washed with aqueous Na₂CO₃ (½ saturated, 2×250 mL) in a separatory funnel. The oil then formed a solid in the separatory funnel. The solid was collected by vacuum filtration. The layers were separated and the organic phase was dried over MgSO₄. The solution was clarified and the solvent was removed in vacuo (3.19 g, ca. 0.0030 mol). The solid obtained from the basic washes was taken up in MeOH and caused to precipitate with the addition of ether (6.35 g, ca. 0.0058 mol, ca. 50%). The ¹H NMR spectrum of this material was consistent with a single hexapeptide product 28 containing small amounts of dicyclohexylurea.

The above procedure to produce 28 was basically repeated. Dicyclohexylcarbodiimide (24 ca. 16 g, ca. 77 mmol) was added to a 3° C. solution of 20 (28.14 g, 51.5 mmol), 13 (33.08 g, 57.2 mmol) and N-hydroxysuccinimide (13.5 g, 117 mmol) in dry DMF (800 mL). The resulting reaction mixture was allowed to stir for 4 days at 3°-5° C. After this period of time, HPLC analysis indicated that the two tripeptides were present at relative intensities of less than 5% (280 nm). Water (ca. 200 mL) was added to the reaction mixture and the resulting solution was filtered to remove precipitated dicyclohexylurea. The clarified solution was concentrated in vacuo to a viscous oil. Additional water was added and the resulting mixture was reconcentrated in vacuo to a viscous oil. Ethyl acetate (400 mL) and aqueous half-saturated sodium carbonate were added to this oil in a 1 L flask. This flask was swirled for 30 minutes on a rotary evaporator (ca. 100 mm, 25° C.) to produce a thick gelatinous precipitate. This precipitate was collected by filtration and the filter cake was washed sequentially with half-saturated sodium carbonate (250 mL), water (6×250 mL) and ethyl acetate (2×500 mL). The resulting solid was dried under high vacuum to constant weight to provide 28 (52.3 g, ca. 47 mmol, ca. 90%). In addition to 28, $^1$H NMR indicated the presence of significant amounts of dicyclohexylurea in this solid. This material was not further purified prior to hydrogenation to 36.

FDMS=1107 (M+1 of nominal mass)

F. Preparation of Heptapeptide From Hexapeptide Intermediate

His-D-Trp-Ala-Trp-D-Phe-Lys(Boc)-NH$_2$, 36

Palladium on carbon (5%, 12 g) was added to a solution containing peptide 28 (51.7 g, ca. 47 mmol) in methanol (1 L) under an inert atmosphere of argon. Hydrogen was bubbled through the reaction mixture for approximately 15 minutes before the reaction was sealed under a hydrogen atmosphere (ca. 1 bar) with an attached hydrogen ballast. The hydrogen ballast was changed every one to two days and on day 4 and day 8 an additional charge of palladium on carbon (4 g each) was added to the reaction mixture. The pyrophoric catalyst was only added after argon had been bubbled through the reaction mixture for half an hour. After the addition of catalyst, the reaction was reinitiated by bubbling through hydrogen. After a period of 262 hours (ca. 11 days), HPLC analysis indicated the relative intensity of starting material at less than 2% (214 nm). The reaction mixture was then filtered through Celite ® and the resulting solution was concentrated in vacuo to constant weight to provide 36 (34.74 g, ca. 36 mmol, ca. 77%) as a pale yellow solid which was not further Purified.

FDMS=995 [972(nominal mass)+$^{23}$Na]

(Boc)$_2$Lys-His-D-Trp-Ala-Trp-D-Phe-Lys(Boc)-NH$_2$, 37

Bis-Boc-Lysine N-hydroxysuccinimide ester (31) (9.4 g, ca. 21 mmol) was added to a room temperature solution of peptide 36 (15.6 g ca. 16 mmol) in DMF (500 mL). After a period of 18 hours, an additional portion of the ester 31 (5.15 g, ca. 12 mmol) was added to the reaction mixture. After a total of 42 hours, a third portion of ester 31 (6 g, ca. 14 mmol) was added to the reaction mixture. Although a peak persisted in the HPLC trace of this reaction mixture (ca. 12-25% of the integrated UV absorptions at 275 nm) at the location expected for starting material (36), no change in the HPLC trace for this reaction mixture was observed after the latter two additions of ester 31. After a total of 66 hours, water (100 mL) was added to the reaction mixture and the resulting suspension was filtered to remove particulates. The clarified filtrate was concentrated to a viscous oil in vacuo. Ethyl acetate (400 mL) and aqueous half-saturated sodium carbonate (400 mL) were added to this oil in a 1 L flask. The resulting mixture was swirled at room temperature for ten minutes on a rotary evaporator (ca. 100 mm) to cause copious precipitation of a gelatinous solid. This solid was collected by filtration and washed sequentially with water (6×200 mL) and ethyl acetate (300 mL). This solid was dried to constant weight in vacuo to provide a partially purified sample of 37 (10.49 g, ca. 8.1 mmol). The filtrates from the above filtration were combined and the ethyl acetate layer was isolated. The ethyl acetate solution was concentrated in vacuo to a viscous oil. This oil was dissolved in methanol (200 mL) and precipitated by addition of ether (800 mL). The resulting solid was collected by filtration and dried in vacuo to provide a second sample of 37 (2.75 g, ca. 2.1 mmol). The filtrate from this precipitation was concentrated in vacuo to a viscous oil which was set aside for later use. The solid samples of 37 were not further purified but were instead combined and used in the preparation of 35.

FDMS=1301 (M+ of nominal mass)

Lys-His-D-Trp-Ala-Trp-D-Phe-Lys(Boc)-NH$_2$, 35

The protected heptapeptide 37 (12.33 g, ca. 9.5 mmol) was added to a room temperature solution of trifluoroacetic acid (TFA, 154 mL), 1,2-ethanedithiol (35 mL), anisole (11 mL), dimethylsulfide (70 mL) and methylene chloride (77 mL). The resulting solution was allowed to stir for twenty minutes before the crude product was precipitated by addition of ether (2.5 L) to the reaction mixture. The hygroscopic precipitate was isolated by filtration and was dissolved in water (250 mL). The resulting solution was applied to a glass chromatography column (80 mm ID x 60 cm) containing E. Merck Lichroprep RP-18 column packing material (C-18, 25–40 um, irregular mesh, 500 g) which had been preequilibrated with 80% water (containing 0.2% TFA) and 20% methanol (ca. 3L). The column was pressurized with nitrogen (ca. 1-2 bar) and eluted at a flow rate of approximately 2 L per hour with the following water (containing 0.2% TFA)/methanol mixtures: 80/20 (1.5 L), 75/25 (3 L), 70/30 (3 L), 65/35 (4 L), 60/40 (6 L). Analyses by HPLC indicated that 35 eluted at methanol concentrations of 35% and 40%. The appropriate fractions were combined, concentrated in vacuo and lyophilized to provide EP-1 as a fluffy white powder (4.65 g, % peptide 62%, 2.9 mmol). The percent peptide (62±2%) as the free base (excluding trifluoroacetic acid) is the average of the percent peptide content calculated from the carbon and nitrogen analyses, assuming that the peptide was present as the tetratrifluoroacetate salt. The purity of this material was greater than 95% by HPLC (total integrated intensity at 280 nm) and no impurities could be detected in the NMR.

FDMS=1001 (M+1 of nominal mass).

Analysis: Calc for C$_{52}$H$_{68}$N$_{14}$O$_7$.4TFA C,49.45; H,4.98; N,13.46;

Found: C,46.86; H,4.78; N,12.18

An attempt was made to prepare a second batch of 35. The viscous oil containing impure hexapeptide 37 was treated with trifluoroacetic acid, 1,2-ethanedithiol, anisole and dimethylsulfide as above. The crude product was precipitated with ether and combined with impure fractions containing 35 (1.55 g) which were obtained from the chromatography described above. A second chromatography was accomplished on the previously described Lichroprep column using the previous conditions. Appropriate fractions were combined, concentrated in vacuo and lyophilized to provide a second sample of 35 (2.61 g, ca. 1.6 mmol). This material was found to be of approximately 90% purity by HPLC. Proton NMR suggested a purity of greater than 80% for the organic components.

Scheme I
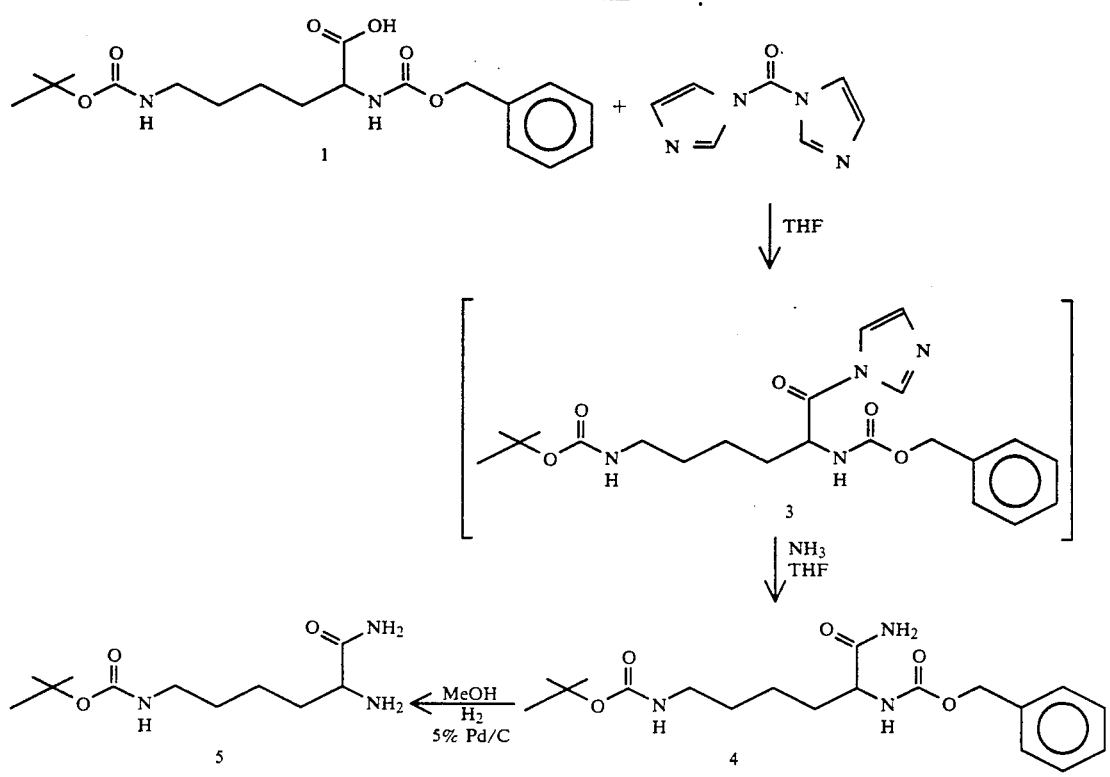
Scheme II
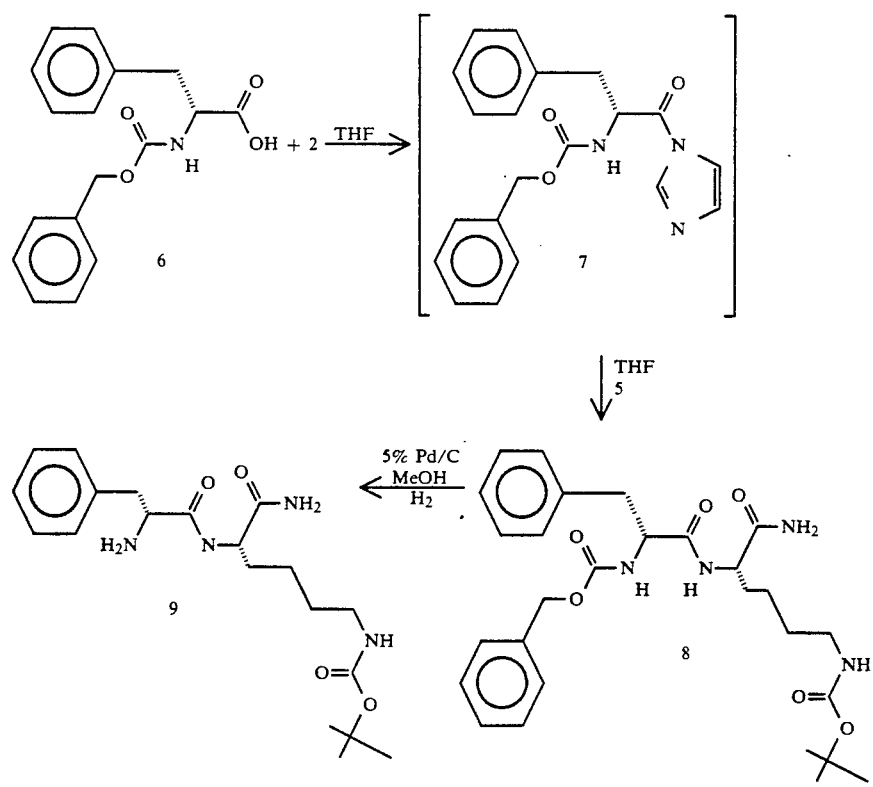

Scheme III
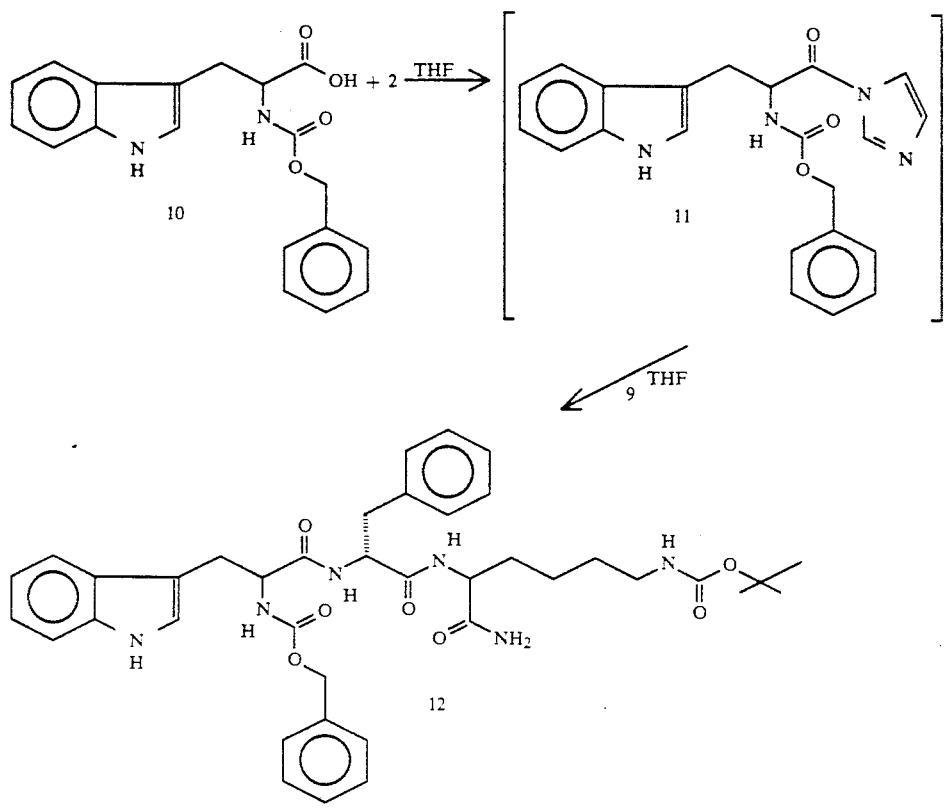
Scheme IV
12
5% Pd/C
MeOH
H₂
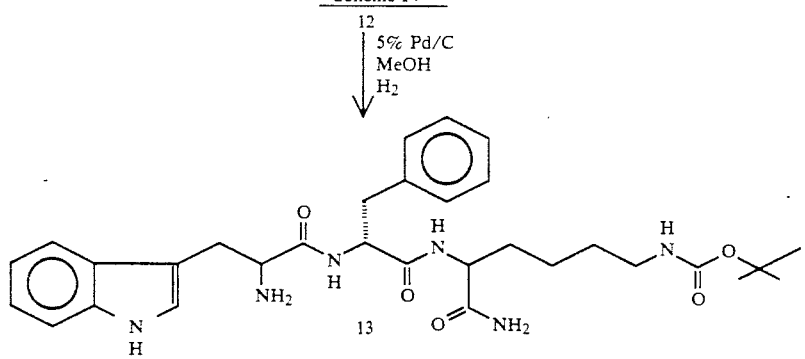

Scheme V
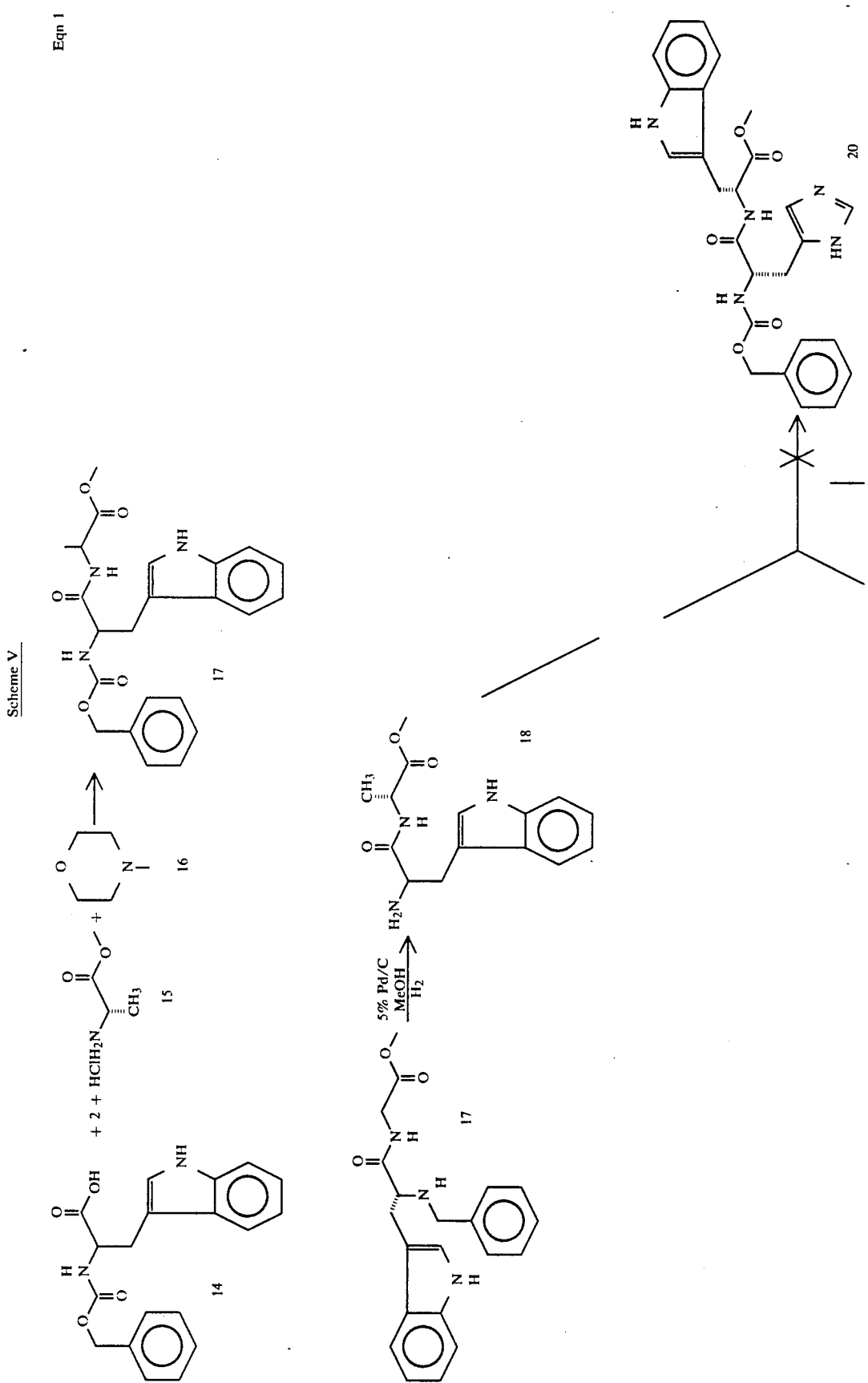
Eqn 1

-continued
Scheme V
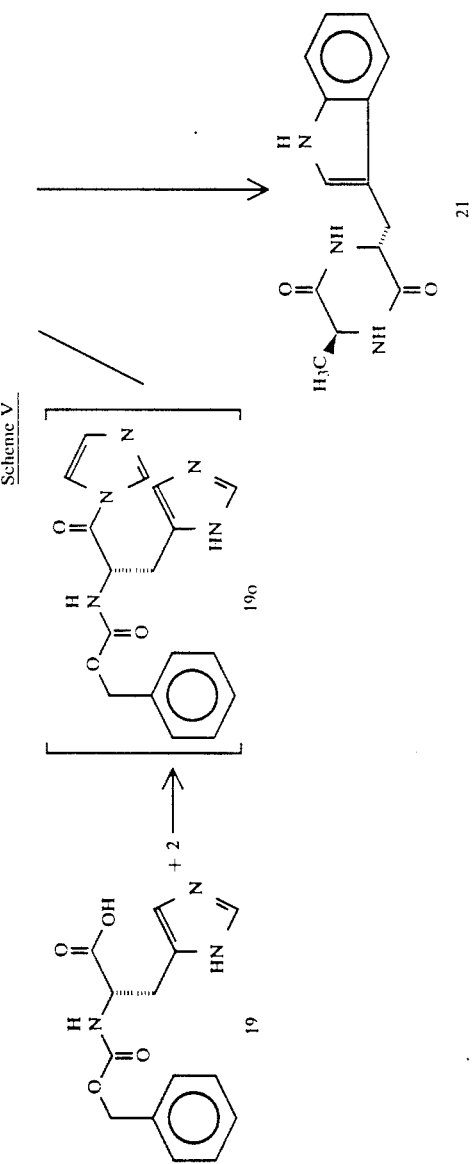

Scheme VI
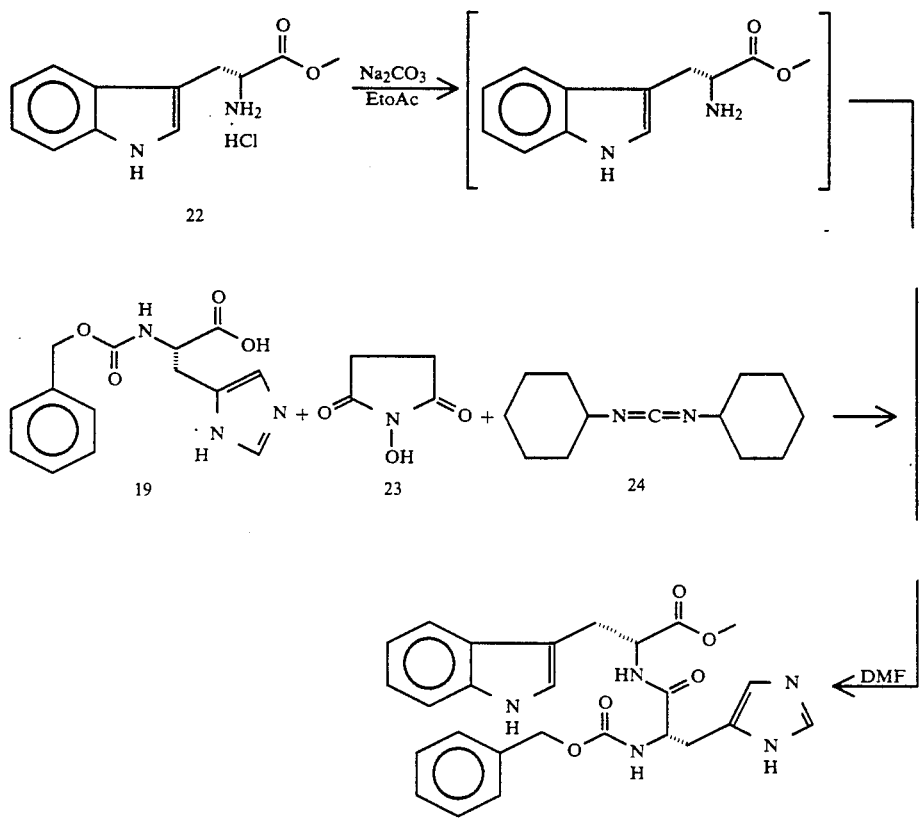
Scheme VII
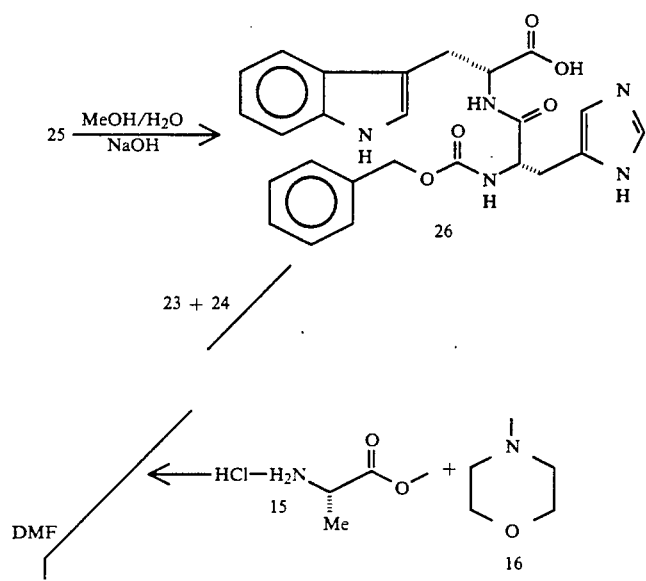

Scheme VII
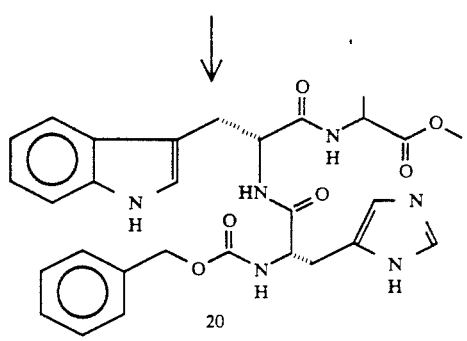
20
Scheme VIII
20
MeOH
H₂O
NaOH
-continued
Scheme VIII
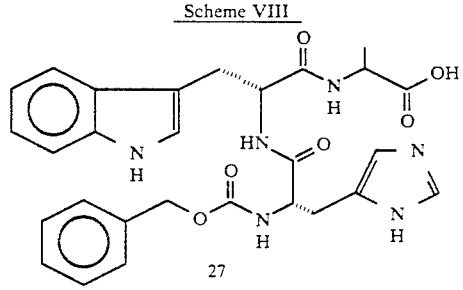
27
Scheme IX
13 + 23 + 24 + 27 → 10° C. / DMF
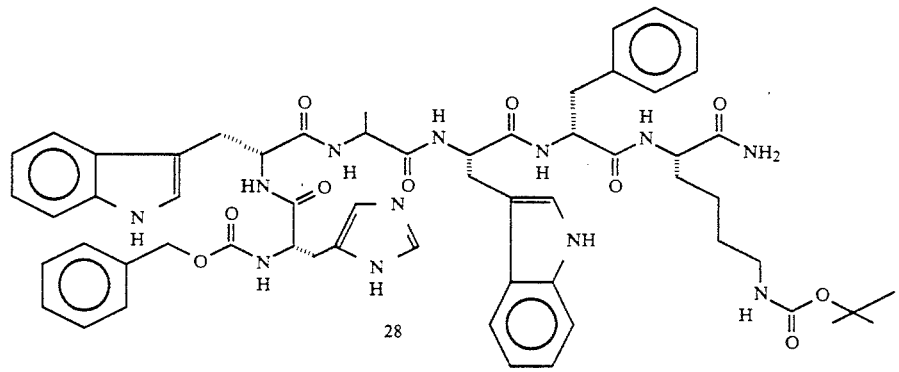
28
Scheme X
CBZ—His—D—Trp—Ala—OMe (20)
↓ H₂ / Pd—C
His—D—Trp—Ala—OMe (30)
↓ Boc—Lys(Boc)—ONSu
Boc—Lys(Boc)—His—D—Trp—Ala—OMe (32)
↓ 1) NaOH
   2) HCl

Scheme X

Boc—Lys(Boc—His—D—Trp—Ala—OH  (33)

↓ DCC, HONSu   2HN—Trp—D—Phe—Lys(Boc)—NH2  (13)

Boc—Lys(Boc)—His—D—Trp—Ala—Trp—D—Phe—Lys(Boc)—NH2  (34)

↓ CF$_3$COOH, Me$_2$S, HSCH$_2$CH$_2$SH, CH$_2$Cl$_2$

Lys—His—D—Trp—Ala—Trp—D—Phe—Lys—NH2  (35)

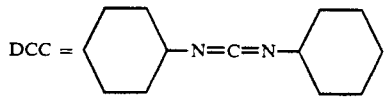

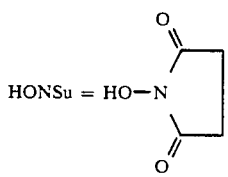

Scheme XI

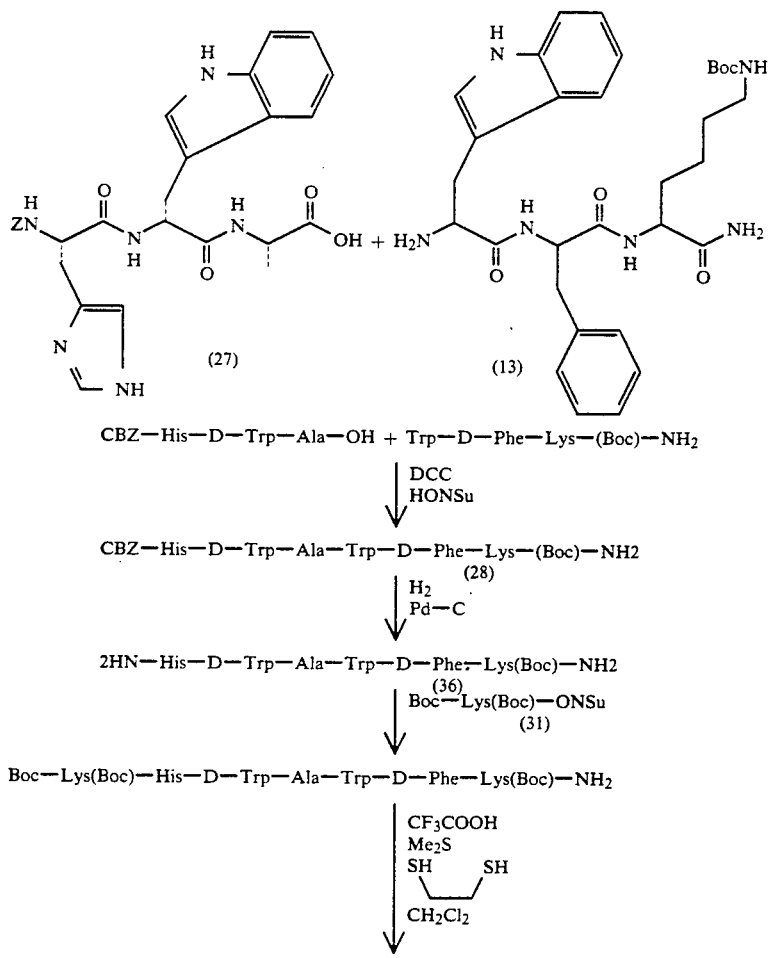

CBZ—His—D—Trp—Ala—OH + Trp—D—Phe—Lys—(Boc)—NH2

↓ DCC, HONSu

CBZ—His—D—Trp—Ala—Trp—D—Phe—Lys—(Boc)—NH2  (28)

↓ H$_2$, Pd—C

2HN—His—D—Trp—Ala—Trp—D—Phe—Lys(Boc)—NH2  (36)

↓ Boc—Lys(Boc)—ONSu  (31)

Boc—Lys(Boc)—His—D—Trp—Ala—Trp—D—Phe—Lys(Boc)—NH2

↓ CF$_3$COOH, Me$_2$S, HSCH$_2$CH$_2$SH, CH$_2$Cl$_2$

Scheme XI

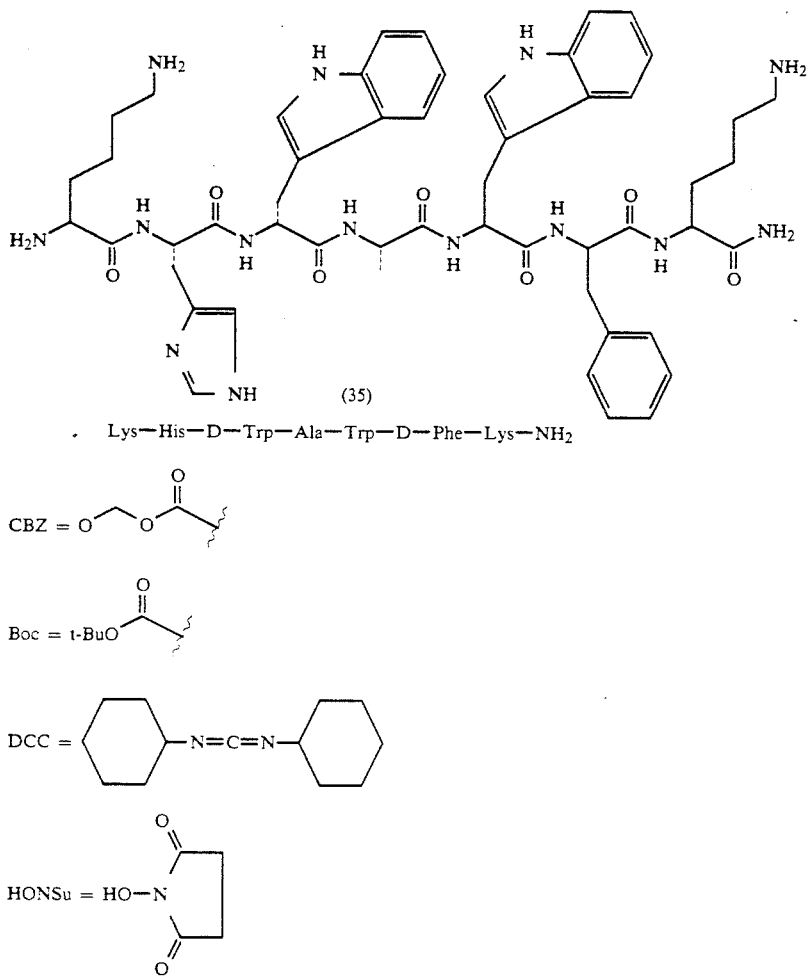

Lys—His—D—Trp—Ala—Trp—D—Phe—Lys—NH$_2$

CBZ = (structure)

Boc = t-BuO-C(=O)-

DCC = cyclohexyl-N=C=N-cyclohexyl

HONSu = HO-N(succinimide)

The invention has been described in detail with particular reference to preferred embodiments thereof. However, it will be appreciated that those skilled in the art, upon consideration of this disclosure, may make variations and modifications within the spirit and scope of the invention.

We claim:

1. A method for forming a substantially pure protected peptide of the formula A$_1$—A$_2$—A$_3$—A$_4$—A$_5$—A$_6$—A$_7$ which comprises:
reacting a peptide fragment of the formula

X—A$_2$—Y with a peptide fragment of the formula

U—V—W in a polar solvent which solubilizes the two fragments, in the presence of a dehydrating agent and activating agent under conditions sufficient for the fragments to react, wherein said X—A$_2$—Y is Prot-A$_1$(protecting group)-A$_2$—A$_3$—A$_4$—OH and further wherein A$_1$ is Ala or Lys, A$_2$ is His, A$_3$ is DTrp, DPhe, D$^\beta$Nal or D$^\alpha$Nal, and A$_4$ is Ala, and wherein said U—V—W is 2NH—A$_5$—A$_6$—A$_7$(-protecting group)—NH$_2$, further wherein A$_5$ is Trp, A$_6$ is DPhe and A$_7$ is Lys, and said substantially pure protected peptide is separated by precipitation.

2. The method of claim 1 wherein a peptide of the formula (Boc)—Lys(Boc)—His—D—Trp—Ala—Trp—D—Phe—Lys(Boc)—NH$_2$is formed, which comprises reacting a peptide fragment of the formula (Boc)—Lys(Boc)—His—D—Trp—Ala with a peptide fragment of the formula Trp—D—Phe—Lys(Boc)—NH$_2$ in a suitable solvent in the presence of a dehydrating agent and activating agent under conditions sufficient for the fragments to react which involves subsequent to reaction the precipitative purification of (Boc)—Lys(Boc)—His—D—Trp—Ala—Trp—D—Phe—Lys(Boc)—NH$_2$.

3. The method of claim 2 wherein said solvent is dimethylformamide solvent, said dehydrating agent is a carbodiimide and said activating agent is N-hydroxysuccinimide.

4. The method of claim 3 wherein the reaction proceeds at a reaction temperature of −10° to 30° C. and wherein, subsequent to said reaction, there is precipitative purification from ethyl acetate of (boc)—Lys(Boc)—His—D—Trp—Ala—Trp—D—Phe—Lys—(Boc)—NH$_2$.

5. The method according to claim 3 which additionally involves treatment of the peptide produce, (Boc)—Lys—(Boc)—His—D—Trp—Ala—Trp—D—Phe—Lys—(Boc)—NH$_2$, under acidic conditions to form a peptide of the formula Lys—His—D—Trp—Ala—Trp—D—Phe—Lys—NH$_2$.

6. The method of claim 1, wherein a racemization inhibitor is also added to the solvent.

7. A method of claim 6 wherein said racemization inhibitor is 1-hydroxybenzotriazole or N-hydroxysuccinimide.

8. A method of forming a substantially pure protected peptide of the formula benzyloxycarbonyl-His—D—Trp—Ala—Trp—D—Phe—Lys(Boc)—NH$_2$ which comprises reacting a peptide fragment of the formula benzyloxycarbonyl-His—D—Trp—Ala with a peptide fragment of the formula Trp—D—Phe—Lys(Boc)—NH$_2$ in a polar solvent in the presence of a dehydrating agent and activating agent under conditions sufficient for the fragments to react which involves subsequent to reaction the precipitative purification of benzyloxycarbonyl-His—D—Trp—Ala—Trp—D—Phe—Lys(Boc)—NH$_2$.

9. The method according to claim 8 wherein said solvent is dimethylformamide, said dehydrating agent is a carbodiimide and said activating agent is N-hydroxysuccinimide.

10. The method of claim 9 wherein the reaction proceeds at a reaction temperature of −10° to 30° C. and wherein, subsequent to said reaction, there is precipitative purification from ethyl acetate of benzyloxycarbonyl-His—D—Trp—Ala—Trp—D—Phe—Lys(Boc)—NH$_2$ under neutral or alkaline conditions.

11. A method according to claim 9 which additionally involves treatment of the peptide product, benzyloxycarbonyl-His—D—Trp—Ala—Trp—D—Phe—Lys—(Boc)—NH$_2$, under reductive conditions and under acidic conditions to form a peptide of the formula His—D—Trp—Ala—Trp—D—Phe—Lys—NH$_2$.

12. A method of claim 8 wherein a racemization inhibitor is also added to the solvent.

13. A method of claim 12 wherein the racemization inhibitor is 1-hydroxy-benzotriazole or N-hydroxysuccinimide.

14. The method for forming a substantially pure protected peptide of the formula $A_2$—$A_3$—$A_4$—$A_5$—$A_6$—$A_7$ which comprises:
reacting a peptide fragment of the formula $$X-A_2-Y$$

with a peptide of the formula $$U-V-W$$

in a polar solvent which solubilizes the two fragments, in the presence of a dehydrating agent and activating agent under conditions sufficient for the fragments to react,
wherein said U—V—W is 2NH—$A_5$—$A_6$—$A_7$(protecting group)—NH$_2$ and further wherein $A_5$ is Trp, $A_6$ is DPhe and $A_7$ is Lys, and
wherein X—$A_2$—Y is (protecting group)—$A_2$—$A_3$—$A_4$—OH
wherein A2 is His, $A_3$ is DTrp, DPhe, D$^\beta$Nal or D$^\alpha$Nal, and $A_4$ is Ala, and said substantially pure protected peptide is separated by precipitation.

15. The method of claim 14 wherein X—$A_2$—Y is CBZ—His—DTrp—Ala.

16. A method of claim 14 wherein a racemization inhibitor is added to the solvent.

17. A method of claim 16 wherein said racemization inhibitor is 1-Hydroxybenzotriazole or N-Hydroxysuccinimide.

* * * * *

UNITED STATES PATENT AND TRADEMARK OFFICE
CERTIFICATE OF CORRECTION

PATENT NO. : 5,322,931
DATED : June 21, 1994
INVENTOR(S) : John C. Hubbs, et al.

It is certified that error appears in the above-indentified patent and that said Letters Patent is hereby corrected as shown below:

Column 41, line 67 (Claim 1, line 20), please delete "2NH" and insert "2HN" therefor.

Column 41, line 67 (Claim 1, line 20), please delete the "-" at the end of the line.

Column 42, line 66 (Claim 4, line 4), please delete "(boc)" and insert " $_{Boc}$ " therefor.

Column 44, line 15 (Claim 14, line 8), please insert the word "fragment" after the word "peptide".

Column 44, line 23 (Claim 14, line 16), please delete "2NH" and insert "2HN" therefor.

Signed and Sealed this

Twenty-seventh Day of September, 1994

Attest:

BRUCE LEHMAN

Attesting Officer

Commissioner of Patents and Trademarks